US009843004B2

(12) United States Patent
Pan et al.

(10) Patent No.: US 9,843,004 B2
(45) Date of Patent: Dec. 12, 2017

(54) METAL-LIGAND COORDINATION COMPOUNDS

(71) Applicant: Merck Patent GmbH, Darmstadt (DE)

(72) Inventors: Junyou Pan, Frankfurt am Main (DE); Rémi Manouk Anémian, Seoul (KR); Herwig Buchholz, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 274 days.

(21) Appl. No.: 14/850,518

(22) Filed: Sep. 10, 2015

(65) Prior Publication Data

US 2015/0380649 A1 Dec. 31, 2015

Related U.S. Application Data

(63) Continuation of application No. 13/825,606, filed as application No. PCT/EP2011/004417 on Sep. 1, 2011, now abandoned.

(30) Foreign Application Priority Data

Sep. 23, 2010 (DE) .................. 10 2010 046 412

(51) Int. Cl.
*H01L 51/00* (2006.01)
*C07F 15/00* (2006.01)
*C09K 11/06* (2006.01)
*H01L 51/50* (2006.01)

(52) U.S. Cl.
CPC ........ *H01L 51/009* (2013.01); *C07F 15/0033* (2013.01); *C07F 15/0086* (2013.01); *C09K 11/06* (2013.01); *H01L 51/0085* (2013.01); *C09K 2211/1011* (2013.01); *C09K 2211/1029* (2013.01); *C09K 2211/185* (2013.01); *H01L 51/5016* (2013.01); *Y02E 10/549* (2013.01)

(58) Field of Classification Search
CPC ............... H01L 51/0085; H01L 51/009; C07F 15/0033; C07F 15/0086; Y02E 10/549
See application file for complete search history.

(56) References Cited

U.S. PATENT DOCUMENTS

| | | | | |
|---|---|---|---|---|
| 6,989,273 B2 * | 1/2006 | Hsieh | .................. | C07F 15/0033 428/212 |
| 7,820,822 B2 * | 10/2010 | Fortte | ................. | C07F 15/0033 428/689 |
| 7,973,168 B2 * | 7/2011 | Suh | ..................... | C07F 15/0033 313/504 |
| 2004/0138455 A1 | 7/2004 | Stossel et al. | | |
| 2006/0127696 A1 * | 6/2006 | Stossel | ................ | C07F 15/0033 428/690 |

FOREIGN PATENT DOCUMENTS

| | | |
|---|---|---|
| JP | 2003-073666 A | 3/2003 |
| JP | 2004-075681 A | 3/2004 |
| JP | 2005187473 A | 7/2005 |
| JP | 2005528759 A | 9/2005 |
| JP | 2005325048 A | 11/2005 |
| JP | 2006316162 A | 11/2006 |
| JP | 2007254540 A | 10/2007 |
| JP | 2007277170 A | 10/2007 |
| JP | 2008504371 A | 2/2008 |
| JP | 2009130094 A | 6/2009 |
| JP | 2009302152 A | 12/2009 |
| JP | 2010165768 A | 7/2010 |
| WO | WO-02068435 A1 | 9/2002 |

OTHER PUBLICATIONS

International Search Report for PCT/EP2011/004417, dated Jan. 23, 2012.
Maekawa, Masahiko, et al., "Syntheses and Crystal Structures of the First Iridium Complexes with m- and p-terphenyl (tp)", Inorganic Chimica Acta, vol. 357, (2004), pp. 331-338.
English Translation of First Office Action in JP 2013-529567 dated Apr. 28, 2015.

* cited by examiner

*Primary Examiner* — Peter F Godenschwager
*Assistant Examiner* — Andrew J Oyer

(57) ABSTRACT

The present invention relates to novel metal-ligand coordination compounds of the general formula T1-(A-T2)i, where T1 and T2 represent metal-ligand coordination compounds, to the use thereof in a device, and to a formulation and a device which comprise the novel compounds.

21 Claims, No Drawings

METAL-LIGAND COORDINATION COMPOUNDS

CROSS-REFERENCE TO RELATED APPLICATIONS

This application is a continuation application, and claims benefit under 35 U.S.C. §120, of U.S. application Ser. No. 13/825,606, filed Mar. 22, 2013, which in turn claims benefit to National Stage Application PCT/EP2011/004417, filed Sep. 1, 2011 which in turn claims priority to German Application number 10 2010 046 412.0 which was filed on Sep. 23, 2010, the applications of which are incorporated herein by reference in their entirety.

The present invention relates to novel metal-ligand coordination compounds of the general formula $T^1$-$(A$-$T^2)_i$, where $T^1$ and $T^2$ represent metal-ligand coordination compounds, to the use thereof in an electronic device, and to a formulation and an electronic device which comprise the novel compounds.

BACKGROUND OF THE INVENTION

Electronic devices which comprise organic, organometallic and/or polymeric semiconductors are being used ever more frequently in commercial products or are just about to be introduced onto the market. Examples which may be mentioned here are organic-based charge-transport materials (in general triarylamine-based hole transporters) in photocopiers and organic or polymeric light-emitting diodes (OLEDs or PLEDs) in display devices or organic photoreceptors in copiers. Organic solar cells (O-SCs), organic field-effect transistors (O-FETs), organic thin-film transistors (O-TFTs), organic integrated circuits (O-ICs), organic optical amplifiers or organic laser diodes (O-lasers) are also at an advanced stage of development and may achieve major importance in the future.

Many of these electronic and opto-electronic devices have, irrespective of the particular application, the following general layer structure, which can be adapted to the particular application:

(1) substrate,
(2) electrode, frequently metallic or inorganic, but also made from organic or polymeric conductive materials;
(3) charge-injection layer or interlayer for compensation of unevenness of the electrode ("planarisation layer"), frequently made from a conductive, doped polymer,
(4) organic semiconductors,
(5) possibly a further charge-transport or charge-injection or charge-blocking layer,
(6) counterelectrode, materials as mentioned under (2),
(7) encapsulation.

The above arrangement represents the general structure of an opto-electronic device, where various layers can be combined, so that, in the simplest case, an arrangement comprising two electrodes, between which an organic layer is located, results. The organic layer in this case fulfils all functions, including the emission of light. A system of this type is described, for example, in WO 9013148 A1 based on poly(p-phenylenes).

A problem which arises in a "three-layer system" of this type is, however, the lack of a possibility to optimise the individual constituents in different layers with respect to their properties, as is solved easily, for example, in the case of SMOLEDs ("small-molecule OLEDs") through a multi-layered structure. A "small molecule OLED" consists, for example, of one or more organic hole-injection layers, hole-transport layers, emission layers, electron-transport layers and electron-injection layers as well as an anode and a cathode, where the entire system is usually located on a glass substrate. An advantage of a multilayered structure of this type consists in that various functions of charge injection, charge transport and emission can be divided into the various layers and the properties of the respective layers can thus be modified separately.

The layers in SMOLED devices are usually applied by vapour deposition in a vacuum chamber. However, this process is complex and thus expensive and is unsuitable, in particular, for large molecules, such as, for example, polymers, but also for many small molecules, which frequently decompose under the vapour-deposition conditions.

The application of layers from solution is therefore advantageous, where both small molecules and also oligomers or polymers can be processed from solution.

In the conventional process for OLED production, both by deposition from the gas phase or solution-processed, it is difficult to control the distribution of the individual components. The components are usually distributed randomly. This is undesired for some physical properties of such systems, for example in the case of so-called "double doping" in triplet systems (see Kawamura, Y.; Yanagida, S.; Forrest, S. R., "Energy transfer in polymer electro phosphorescent light emitting device with single and multiple doped luminescent layers", J. Appl. Phys., 92 (1), 87-93, 2002). It is reported therein that a very efficient polymer (PHOLED) is produced by using poly(9-vinylcarabazole) (PVK) as host molecule, which is doped with one or more phosphorescent cyclometallated Ir(III) complexes. It is usually assumed that energy transfer, for example by the Förster mechanism, takes place in the case of double doping.

The Förster energy transfer rate $\Gamma_{DA}$ can be represented theoretically, for example, by the following formula:

$$\Gamma_{DA} \propto 1/R^6,$$

where R represents the separation between donor and acceptor. This separation is usually also known as the Förster radius. In order to facilitate efficient energy transfer, for example by Förster energy transfer or others, it is thus necessary to position the donor and acceptor, i.e. the two emitter compounds or metal complexes, as close as possible, advantageously within the so-called Förster radius.

The fact that the two emitters are usually distributed randomly means that the requisite small separation of the two emitter molecules from one another (donor and acceptor) is not guaranteed to the full extent.

DETAILED DESCRIPTION OF THE INVENTION

A further major problem in the case of solution-based SMOLEDs is the film-formation property. The materials used are frequently very readily soluble in a solvent and can be applied to the substrate, for example, by ink-jet printing. However, many materials do not exhibit good film-formation properties, caused by the high mobility of the small molecules in the solvent.

The object of the present invention was therefore to provide novel compounds in which two emitter molecules have the requisite small separation which is necessary for efficient energy transfer between the emitter molecules, so that a random distribution of the two interacting emitter molecules in a layer of an electronic device cannot be present.

For this purpose, the present invention provides a compound of the following formula (1):

   formula (1)

where $T^1$ is an i-valent unit of the formula $M^1(L^1)_n$, and $T^2$ is on each occurrence, identically or differently, a monovalent unit of the formula $M^2(L^2)_m$;

where the symbols and indices used have the following meanings:

A is preferably a divalent unit which contains a conjugation-interrupting unit;

$M^1$ and $M^2$ are preferably selected, independently of one another and identically or differently on each occurrence, from the group consisting of main-group metals, transition metals, lanthanoids and actinoids;

$L^1$ and $L^2$ are preferably, independently of one another and identically or differently on each occurrence, mono- or polydentate organic ligands, so that the units of the formulae $M^1(L^1)_n$ and $M^2(L)^2_m$ represent metal-ligand coordination compounds;

i is preferably an integer greater than or equal to 1;

n and m are preferably, independently of one another, an integer greater than or equal to 2.

It is preferred here for $T^1$ and $T^2$ to be bonded to A via atoms of the ligands $L^1$ and $L^2$, i.e. for the compounds of the formula (1) to contain structural units of the form $L^1$-A-$L^2$. An H atom of an atom of the ligand is preferably not present here, and the corresponding atom of the ligand forms at this point a link to the divalent unit A. In the case of $T^2$, in view of the fact that $T^2$ only occurs once in the compound of the formula (1), only one of the ligands in $T^2$ forms a bond to A. In the case of $T^1$, to which a plurality of units $AT^2$ may also bond, the units $AT^2$ can bond to one of the ligands of $T^1$ or to different ligands of $T^1$, it is preferred that each unit $AT^2$ bonds to different ligands of $T^1$.

In a preferred embodiment of the present invention, the structural units $L^1$-A-$L^2$ occurring in the compounds of the formula (1) contain at least 7, very preferably at least 10, very particularly preferably at least 15 and especially preferably at least 20 non-hydrogen atoms.

In a furthermore preferred embodiment of the present invention, the compounds of the formula (1) contain the said structural units $L^1$-A-$L^2$, where the ligands $L^1$ and $L^2$ present therein are bidendate, tridentate or polydendate, preferably bidendate and tridentate ligands and very particularly preferably bidendate ligands.

Due to the covalent linking of at least two metal-ligand coordination centres $T^1$ and $T^2$ by the conjugation-interrupting unit A, the compound of the formula (1) according to the invention has excellent energy-transfer rates between the two centres $T^1$ and $T^2$.

The term "energy transfer" in the present invention is taken to mean a physical process in which energy is transferred from an excited dye (donor) to a second dye (acceptor) in a radiation-free manner, such as, for example, by Förster transfer (see T. Förster, "Zwischenmolekulare Energiewanderung und Fluoreszenz" [Intermolecular Energy Migration and Fluorescence], Ann. Physic. 437, 1948, 55) or Dexter transfer (see D. L. Dexter, J. Chem. Phys., (1953) 21, 836).

In the present invention, either the unit $T^1$ or the unit $T^2$ can serve as donor, and the respective other unit can serve as acceptor in the sense of the said energy transfer.

In accordance with the invention, the metal coordination compound which emits at shorter wavelength is referred to as donor, and the metal coordination compound which emits at longer wavelength as acceptor.

In a preferred embodiment of the invention, $M^1$ or $M^2$ stand for a transition metal, for a main-group metal or a lanthanide. If $M^1$ or $M^2$ stand for a main-group metal, they then preferably stand for a metal from the third, fourth or fifth main group, in particular for tin. If $M^1$ or $M^2$ is a transition metal, they then preferably stand for Ir, Ru, Os, Pt, Zn, Mo, W, Rh and Pd. Eu is preferred as lanthanide.

Preference is given to compounds of the formula (1) in which $M^1$ or $M^2$ stands for a transition metal, in particular for a tetracoordinated, a pentacoordinated or a hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, platinum, copper and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V); very particular preference is given to Mo(0), W(0), Re(I), Ru(II), Os(II), Rh(III), Ir(III), Pt(II) and Cu(I), in particular Ir(III) and Pt(II).

In a preferred embodiment of the invention, $M^1$ or $M^2$ is a tetracoordinated metal. In this case, n or m can be, independently of one another, an integer between 2, 3 or 4, where it is preferred for n or m to be equal to 2, so that the ligands $L^1$ and $L^2$ are bidentate ligands.

In a further preferred embodiment of the invention, $M^1$ or $M^2$ is a hexacoordinated metal, and the index n or m stands for 2, 3, 4, 5 or 6, preferably for 2 or 3, so that the ligands $L^1$ or $L^2$ can be tridentate or bidentate ligands.

In one embodiment it is preferred for $M^1$ and $M^2$ to be different metals, in a further embodiment it may also be preferred for $M^1$ and $M^2$ to represent the same metal. In the second case, the donor or acceptor properties are crucially determined by the influence of the ligands, which are then very generally not identical in the case of $M^1$ and $M^2$, at least with respect to the entire coordination sphere, i.e. also with respect to tautomerism in the case of identical ligands.

In the structural units of the general formula (1), A is in each case, independently of one another, a divalent unit which contains a so-called nonconjugated spacer or a conjugation-interrupting unit. The divalent unit may also be the so-called conjugation-interrupting unit in its totality. A conjugation-interrupting unit is taken to mean a unit which interferes with or preferably interrupts the conjugation, i.e. a possible conjugation of the ligands $L^1$ and $L^2$ bonded to A is interfered with or preferably interrupted. Conjugation in chemistry is taken to mean the overlap of a π orbital (π=PI) with a p orbital of an $sp^2$-hybridised (carbon) atom or further π orbitals. By contrast, a conjugation-interrupting unit in the sense of this application is taken to mean a unit which interferes with or preferably completely prevents such an overlap. This can take place, for example, by means of a unit in which the conjugation is interfered with by at least one $sp^3$-hybridised atom, preferably carbon. The conjugation can likewise be interfered with by a non-$sp^3$-hybridised atom, for example by N, P or Si.

The divalent unit A is preferably selected from the group consisting of linear or branched $C_{1-12}$-alkylene, $C_{3-8}$-cycloalkylene, linear or branched mono($C_{1-12}$-alkyl)silylene, linear or branched di($C_{1-12}$-alkyl)silylene, linear or branched tri($C_{1-12}$-alkyl)silylene, a silylene group which is substituted by one, two or three mono- or polycyclic aromatic or heteroaromatic ring systems having 5 to 60 aromatic ring atoms, linear or branched $Si_{1-5}$-silylene, linear or branched $C_{1-12}$-alkyloxy-$C_{1-12}$-alkylene, linear or branched aryl-$C_{1-12}$-alkyloxy-$C_{1-12}$-alkylene, where aryl is a mono- or polycyclic aromatic or heteroaromatic ring system having 5 to 60 aromatic ring atoms, linear or branched $C_{1-12}$-alkyl-thio-$C_{1-12}$-alkylene, sulfone, linear or branched $C_{1-12}$-alkylene sulfone, sulfoxide and linear or branched $C_{1-12}$-alkylene sulfoxide, where one or more H atoms of the said groups may be replaced by F, Cl, Br, I, a further $C_{1-12}$-alkyl or $C_{3-8}$-cycloalkyl, where one or more $CH_2$ groups of the alkyl or cycloalkyl may be replaced by heteroatoms, such as NH, O or S, or a mono- or polycyclic aromatic or heteroaromatic ring systems having 5 to 60 aromatic ring atoms, and where one or more $CH_2$ groups of the said groups which represent A may be replaced by a divalent mono- or polycyclic aromatic or heteroaromatic ring system having 5 to 60 aromatic ring atoms, with the proviso that the divalent unit A can bond to the ligands $L^1$ or $L^2$ via any conceivable atom of the unit.

A particularly preferably denotes a linear or branched $C_{1-12}$-alkylene or $C_{1-12}$-alkyloxy-$C_{1-12}$-alkylene, where one or more H atoms may be replaced by F.

Furthermore, A preferably corresponds to a divalent unit of the general formulae (2) to (16).

formula (2)

formula (3)

formula (4)

formula (5)

formula (6)

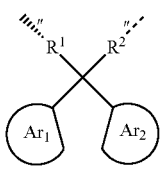

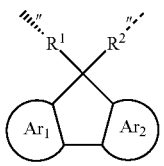

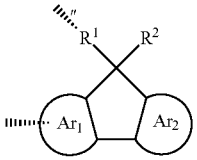

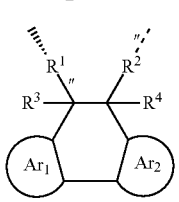

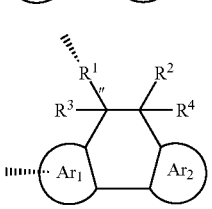

formula (7)

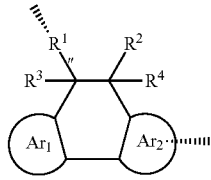

formula (8)

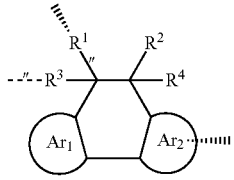

formula (9)

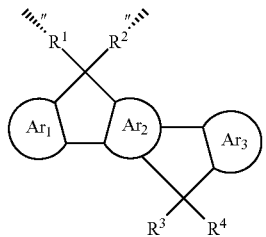

formula (10)

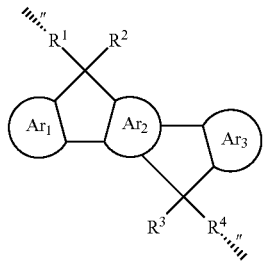

formula (11)

formula (12)

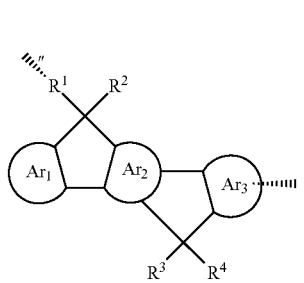

formula (13)

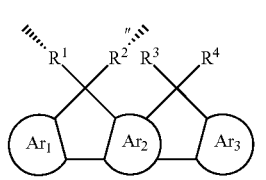

-continued formula (14)

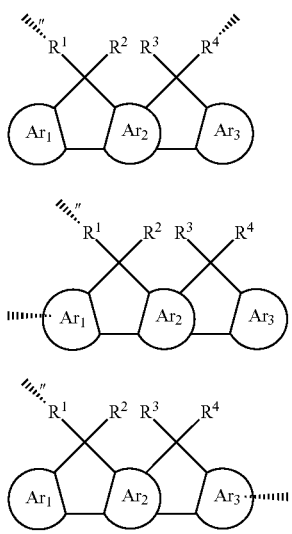

formula (15)

formula (16)

where $Ar_1$, $Ar_2$ and $Ar_3$ each, independently of one another, denote a mono- or polycyclic aromatic or heteroaromatic unit having 5 to 60 ring atoms, two of the radicals $R^1$ to $R^4$ or one of the radicals $R^1$ to $R^4$ and one of the groups $Ar_1$, $Ar_2$ and $Ar_3$ have a bond to the ligands $L^1$ or $L^2$ of the compound of the general formula (1), and where $R^1$, $R^2$, $R^3$ and $R^4$ each, independently of one another, denote alkyl(ene), cycloalkyl(ene), alkylsilyl(ene), silyl(ene), arylsilyl(ene), alkylalkoxyalkyl(ene), arylalkoxyalkyl(ene), alkylthioalkyl (ene), phosphine, phosphine oxide, sulfone, alkylene sulfone, sulfone oxide, alkylene sulfone oxide, where the alkylene group in each case, independently of one another, has 1 to 12 C atoms and where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

The substituents $R^1$ to $R^4$ on the respective $Ar_1$, $Ar_2$ or $Ar_3$ may either be adjacent to one another or one or more ring atoms may be located in between. The atoms to which the substituents $R^1$ to $R^4$ are bonded are preferably ring atoms of the aromatic or heteroaromatic unit.

The following structures of the formula (17) to (31) are particularly preferred for A:

formula (17)

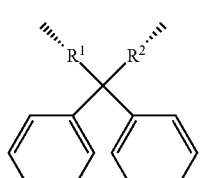

formula (18)

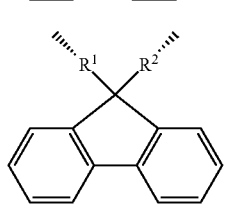

formula (19)

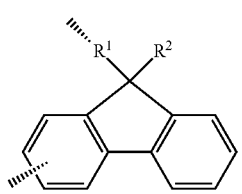

formula (20)

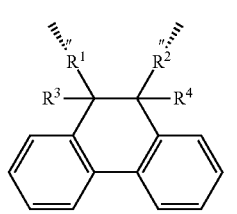

formula (21)

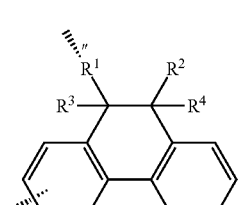

formula (22)

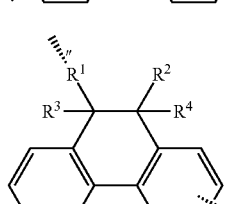

formula (23)

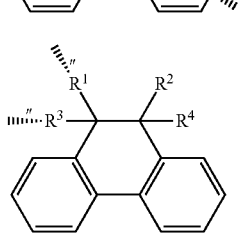

formula (24)

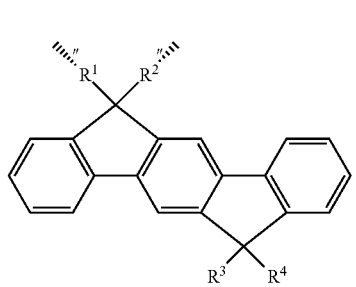

formula (25)

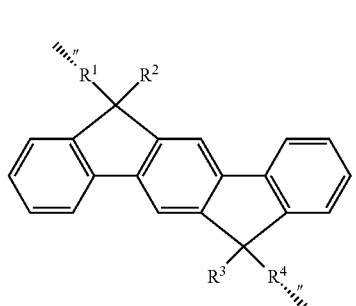

-continued formula (26)
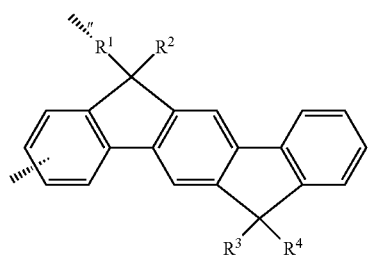

formula (27)
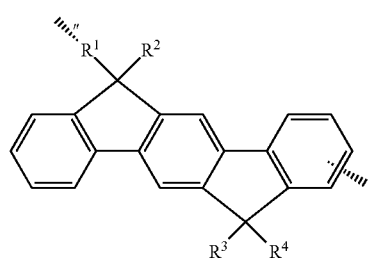

formula (28)
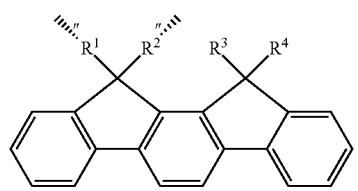

formula (29)
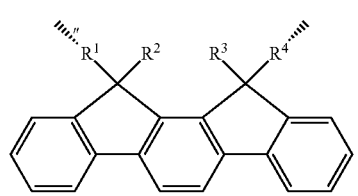

formula (30)
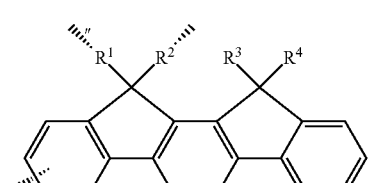

formula (31)
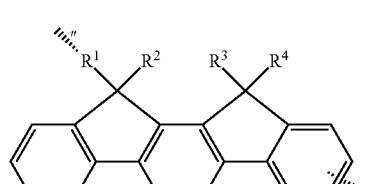

where the symbols and indices have the meaning indicated in the case of the compounds of the formulae (2) to (16).

The following structures, as disclosed, for example, in DE 102009023156.0, are particularly preferred for A:

formula (32)
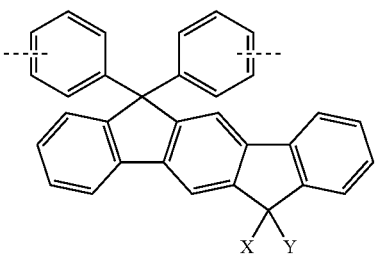

formula (33)
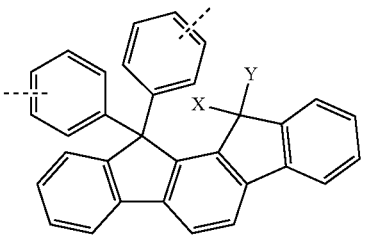

where X and Y are selected, independently of one another, from the group consisting of H, F, $C_{1-40}$-alkyl, $C_{2-40}$-alkenyl, $C_{2-40}$-alkynyl, a substituted or unsubstituted aromatic or heteroaromatic hydrocarbon radical having 5 to 60 ring atoms.

The index i in formula (1) is preferably equal to 1, 2, 3 or 4, more preferably 1, 2 or 3, even more preferably 1 or 2 and most preferably 1.

The index n in formula (1) is preferably equal to 2, 3, 4, 5, 6, 7, 8 or 9, more preferably 2, 3, 4, 5 or 6. If $M^1$ is a hexacoordinated metal, the denticity of the ligands is as follows, depending on n:
  n=2: $M^1$ is coordinated to two tridentate ligands or to one tetradentate and one bidentate ligand or to one pentadentate and one monodentate ligand;
  n=3: $M^1$ is coordinated to three bidentate ligands or to one tridentate, one bidentate and one monodentate ligand or to one tetradentate and two monodentate ligands;
  n=4: $M^1$ is coordinated to two bidentate and two monodentate ligands or one tridentate and three monodentate ligands;
  n=5: $M^1$ is coordinated to one bidentate and four monodentate ligands;
  n=6: $M^1$ is coordinated to 6 monodentate ligands.

It is particularly preferred for $M^1$ to be a hexacoordinated metal, n=3 and $L^1$ to be bidentate ligands in each case.

If $M^1$ is a tetracoordinated metal, the denticity of the ligands is as follows, depending on n:
  n=2: $M^1$ is coordinated to two bidentate ligands or to one tridentate and one monodentate ligand;
  n=3: $M^1$ is coordinated to one bidentate and two monodentate ligands;
  n=4: $M^1$ is coordinated to four monodentate ligands.

The index m is preferably defined in the same way, meaning that the complex $T^2$ can have the same ligand coordination as the complex $T^1$.

The ligands $L^1$ and $L^2$ are preferably neutral, monoanionic, dianionic or trianionic ligands, particularly preferably neutral or monoanionic ligands. They can be monodentate, bidentate, tridentate, tetradentate pentadentate or hexadentate, and are preferably bidentate, i.e. preferably have two coordination sites. The ligands $L^1$ and $L^2$ may also be cationic ligands. The unit A in the compound of the formula (1) may also be electrically charged. In a preferred embodiment of the present invention, A is neutral.

If the compound of the formula (1) contains electrically charged radicals either in $L^1$ and/or in $L^2$ and/or in A, the charges within the compound of the formula (1) must compensate for one another in a very particularly preferred embodiment of the present invention, so that the compound of the formula (1) overall is electrically neutral.

In a preferred embodiment of the present invention, the ligands $L^1$ and $L^2$ and A are electrically neutral.

It is furthermore preferred in accordance with the invention for in each case at least one $L^1$ and/or at least one $L^2$ in the compounds of the formula (1) to be a bidentate ligand.

Preferred neutral, monodentate ligands $L^1$ and $L^2$ are selected from carbon monoxide, nitrogen monoxide, alkylcyanides, such as, for example, acetonitrile, arylcyanides, such as, for example, benzonitrile, alkylisocyanides, such as, for example, methylisonitrile, arylisocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular arduengo carbenes.

Preferred monoanionic, monodentate ligands $L^1$ and $L^2$ are selected from hydride, deuteride, the halides $F^-$, $Cl^-$, $Br^-$ and $I^-$, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups here are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are defined as above.

Preferred di- or trianionic ligands are $O^{2-}$, $S^{2-}$, carbides, which result in coordination in the form R—C≡M, nitrenes, which result in coordination in the form R—N=M, where R generally stands for a substituent, and $N^{3-}$.

Preferred neutral or mono- or dianionic bidentate or polydentate ligands L' are selected from diamines, such as, for example, ethylenediamine, N,N,N',N'-tetramethylethylenediamine, propylenediamine, N,N,N',N'-tetra-methylpropylenediamine, cis- or trans-diaminocyclohexane, cis- or trans-N,N,N',N'-tetra-methyldiaminocyclohexane, imines, such as, for example, 2[1-(phenylimino)ethyl]pyridine, 2[1-(2-methylphenylimino)ethyl]pyridine, 2[1-(2,6-di-iso-propylphenylimino)ethyl]pyridine, 2-[1-(methylimino)ethyl]pyridine, 2-[1-(ethylimino)ethyl]pyridine, 2[1-(iso-propylimino)ethyl]pyridine, 2[1-(tert-butylimino)ethyl]pyridine, diimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl)borate and tetrakis(1-pyrazolyl)borate.

Preference is furthermore given to bidentate monoanionic ligands $L^1$ and $L^2$ which, with the metal, have a cyclometallated five-membered ring or six-membered ring having at least one metal-carbon bond, in particular a cyclometallated five-membered ring. These are, in particular, ligands as generally used in the area of phosphorescent metal complexes for organic electroluminescent devices, i.e. ligands of the phenylpyridine, naphthylpyridine, phenylquinoline, phenylisoquinoline, etc., type, each of which may be substituted by one or more radicals R. A multiplicity of ligands of this type is known to the person skilled in the art in the area of phosphorescent electroluminescent devices, and he will be able to select further ligands of this type as ligand $L^1$ or $L^2$ for compounds of the formula (1). In general, the combination of two groups, as represented by the following formulae (34) to (61), is particularly suitable for this purpose, where one group is bonded via a neutral nitrogen atom or a carbene atom and the other group is bonded via a negatively charged carbon atom or a negatively charged nitrogen atom. The ligand $L^1$ or $L^2$ can then be formed from the groups of the formulae (34) to (61) through these groups bonding to one another, in each case at the position denoted by #. The position at which the groups coordinate to the metal are denoted by *.

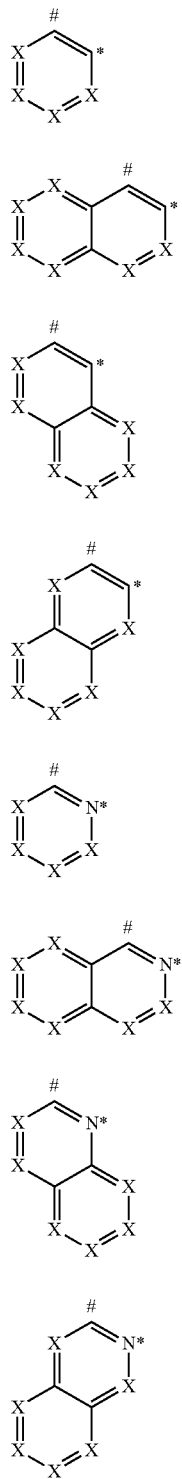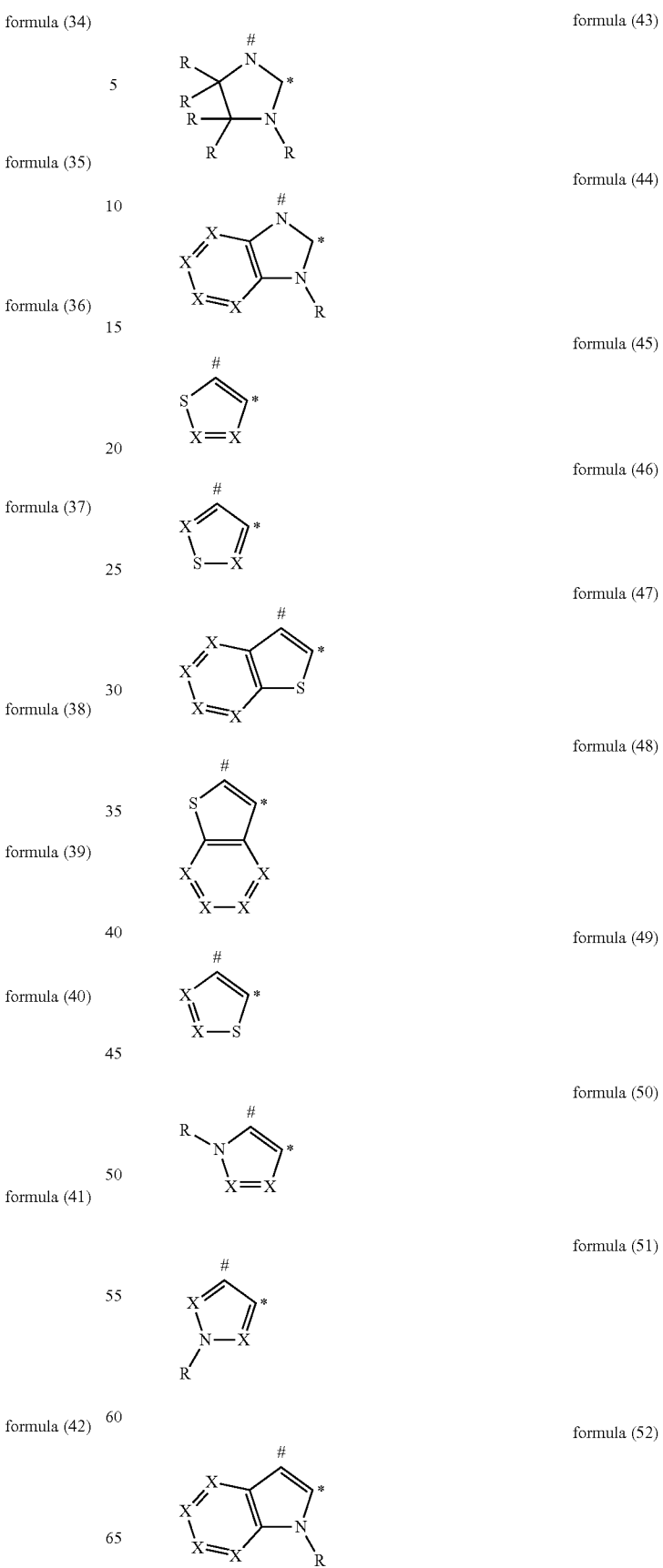

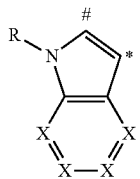

formula (53)

formula (54)

formula (55)

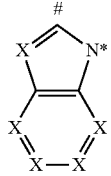

formula (56)

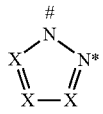

formula (57)

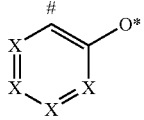

formula (58)

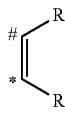

formula (59)

formula (60)

formula (61)

The symbol R here has on each occurrence, identically or differently, the same meaning as $R^1$ to $R^4$ described above and X stands for N or CH. Particularly preferably a maximum of three symbols X in each group stand for N, particularly preferably a maximum of two symbols X in each group stand for N, very particularly preferably a maximum of one symbol X in each group stands for N. Especially preferably, all symbols X stand for CH.

Likewise preferred ligands $L^1$ and $L^2$ are $\eta^5$-cyclopentadienyl, $\eta^5$-penta-methylcyclopentadienyl, $\eta^6$-benzene and $\eta^7$-cycloheptatrienyl, each of which may be substituted by one or more radicals R.

Likewise preferred ligands $L^1$ and $L^2$ are 1,3,5-cis-cyclohexane derivatives, in particular of the formula (62), 1,1,1-tri(methylene)methane derivatives, in particular of the formula (63), and 1,1,1-trisubstituted methanes, in particular of the formulae (64) and (65),

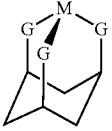

formula (62)

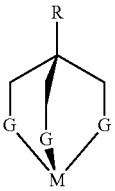

formula (63)

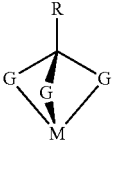

formula (64)

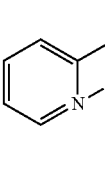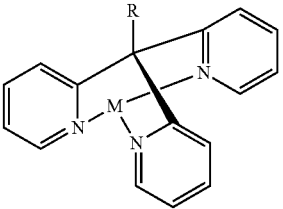

formula (65)

where, in the formulae, the coordination to the metal M (equal to $M^1$ or $M^2$) is depicted, $R^1$ has the meaning mentioned above, and G stands, identically or differently on each occurrence, for $O^-$, $S^-$, $COO^-$, $P(R)_2$ or $N(R)_2$.

The metal-ligand coordination compounds $T^1$ and $T^2$ are preferably neutral complexes, meaning that the compound of the formula (1) is a neutral compound, i.e. the valence of the metals $M^1$ and $M^2$ and the valence of the ligands $L^1$ and $L^2$ is selected so that the charge within each coordination compound is compensated.

In a further preferred embodiment of the present invention, the metal-ligand coordination compounds $T^1$ and $T^2$ are electrically charged, with the proviso that the charges within the compound of the formula (1) neutralize one another, so that the latter is electrically neutral.

The metal-ligand coordination compounds $T^1$ and $T^2$ are preferably phosphorescent emitter units. A phosphorescent emitter is taken to mean a compound which exhibits luminescence from an excited state having relatively high spin multiplicity, i.e. a spin state >1, such as, for example, from an excited triplet state (triplet emitter), from an MLCT mixed state or a quintet state (quintet emitter). Suitable phosphorescent emitter units are, in particular, compounds which emit light, preferably in the visible region, on suitable excitation and in addition contain at least one atom having the atomic numbers >38 and <84, particularly preferably >56 and <80. Preferred phosphorescence emitters are compounds which contain copper, molybdenum, tungsten, rhenium, ruthenium, osmium, rhodium, iridium, palladium, platinum, silver, gold or europium, in particular compounds which contain iridium, platinum or copper. Examples of the emitters described above are revealed by the applications WO 00/7065, WO 2001/41512, WO 2002/02714, WO 2002/15645, EP 1191613, EP 1191612, EP 1191614, WO 2005/033244. In general, all phosphorescent complexes as used in accordance with the prior art for phosphorescent OLEDs and as are known to the person skilled in the art in the area of organic electroluminescence are suitable.

In a further embodiment of the present invention, a compound of the formula (1) in which an emission band of the unit $T^1$ is in a wavelength range which overlaps with the wavelength range of an absorption band of the unit $T^2$ is.

Furthermore, the unit $T^2$ is preferably a dye, where the dyes are preferably metal complexes. These metal complexes are preferably selected from the group consisting of polypyridyl complexes of transition metals, very preferably those containing ruthenium, osmium and copper. In a further preferred embodiment of the present invention, the dye, which is a metal complex, has the general formula $ML^2(X)_2$, where L is preferably selected from the group consisting of 2,2'-bipyridyl-4,4'-dicarboxylic acids and where M is a transition metal, which is preferably selected from the group consisting of Ru, Os, Fe, V and Cu, and where X is selected from the group consisting of halides, cyanides, thiocyanates, acetylacetonates, thiacarbamates or water substituents. Metal complexes of this type are disclosed, for example, in J. Phys. Chem. C 09, 113, 2966-2973, US 2009/000658, WO 2009/107100, WO 2009/098643, U.S. Pat. No. 6,245,988, WO 2010/055471, JP 2010-084003, EP 1622178, WO 98/50393, WO 95/29924, WO 94/04497, WO 92/14741, WO 91/16719.

Examples of compounds of the formula (1) according to the invention are compounds of the following formulae (66) to (111).

formula (66)

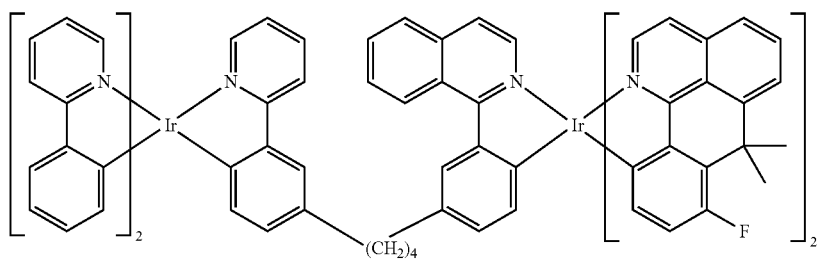

formula (67)

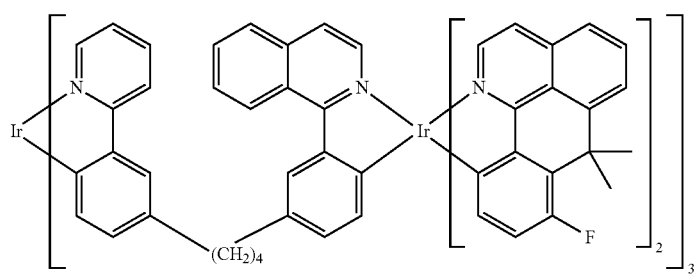

formula (68)

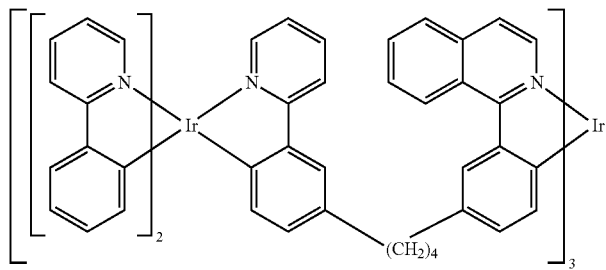

formula (69)

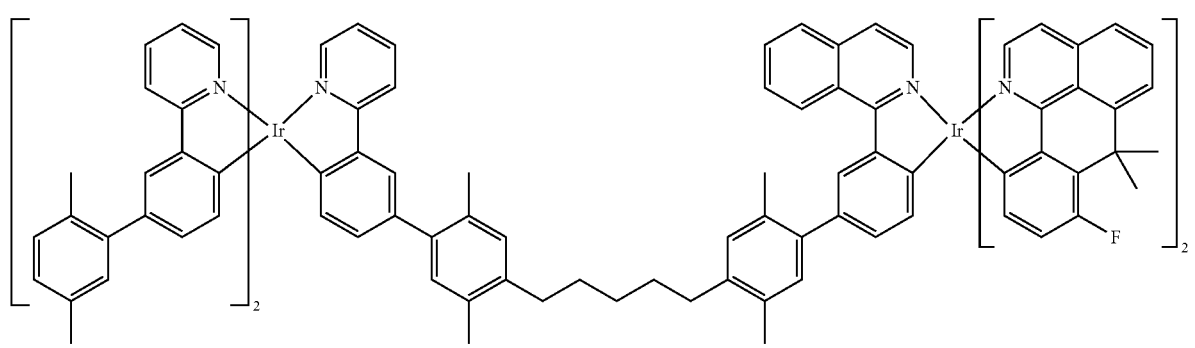

formula (70)
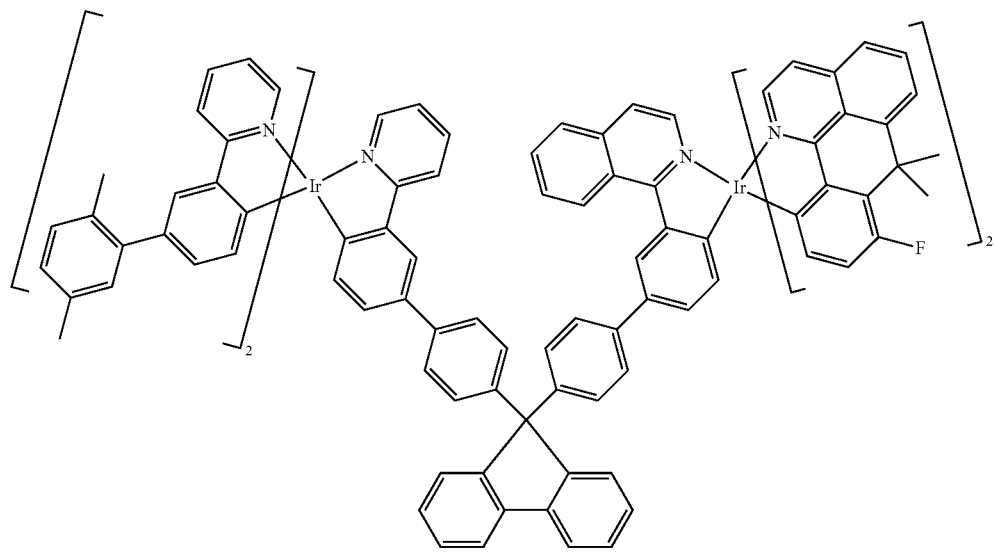
formula (71)
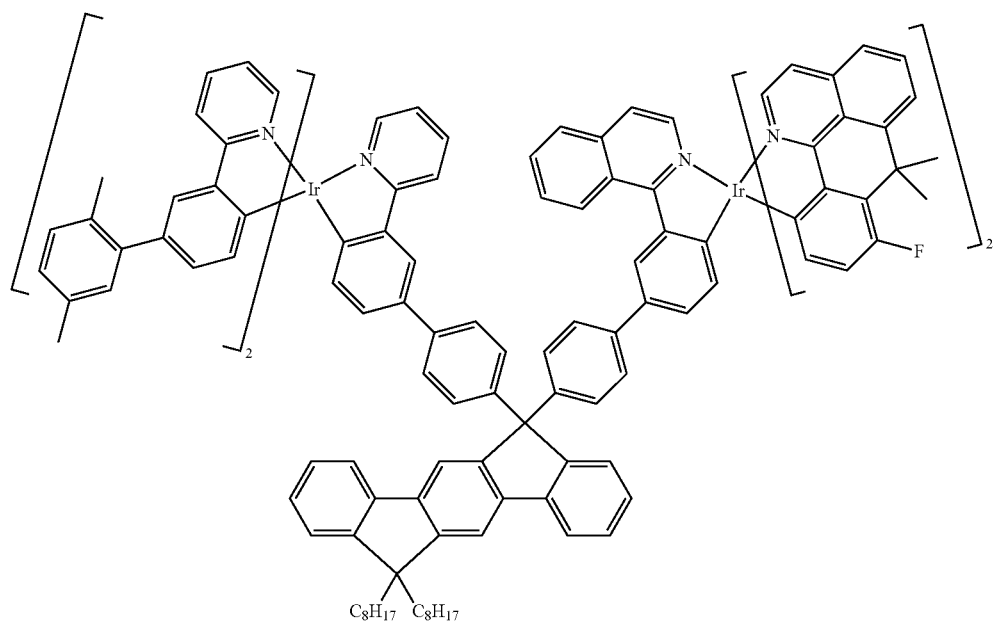
formula (72)
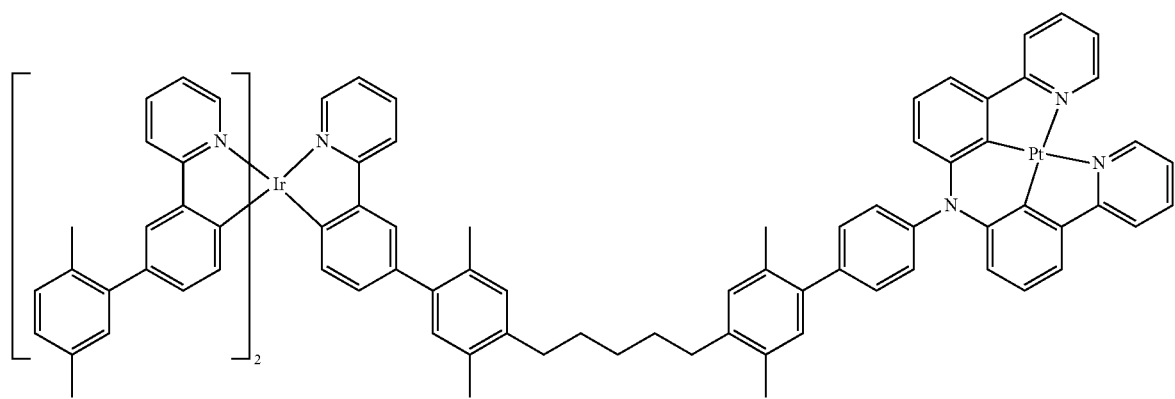

formula (73)
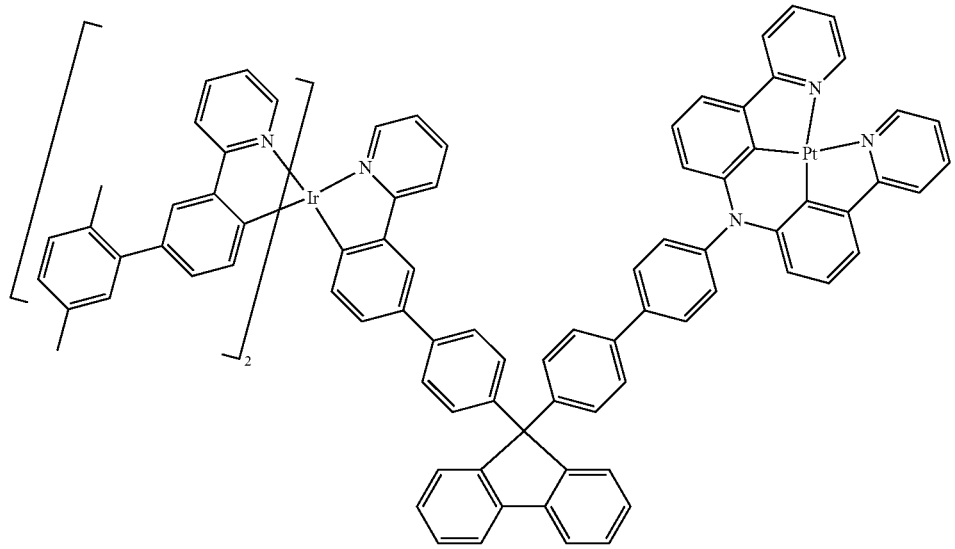
formula (74)
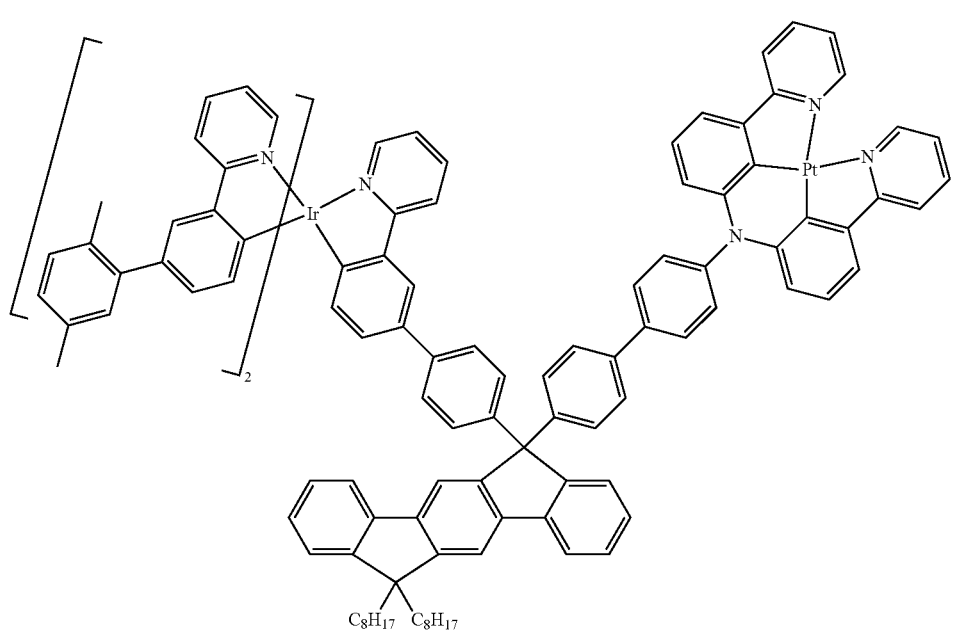
formula (75)
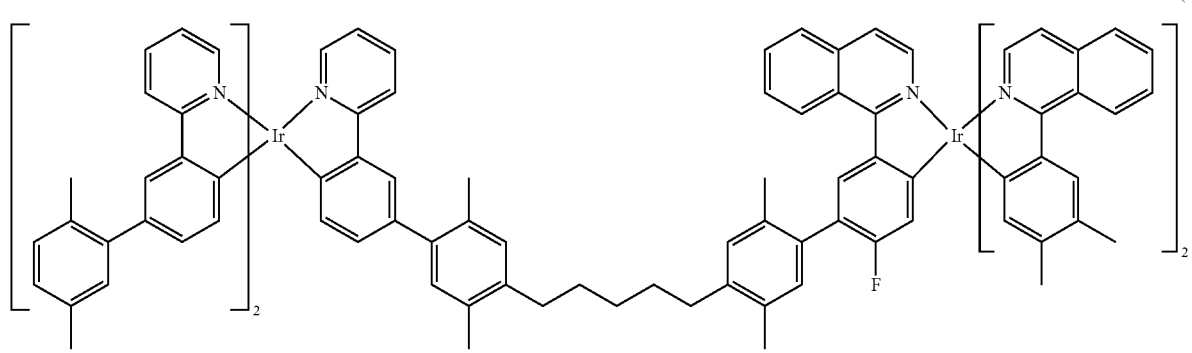

-continued
formula (76)
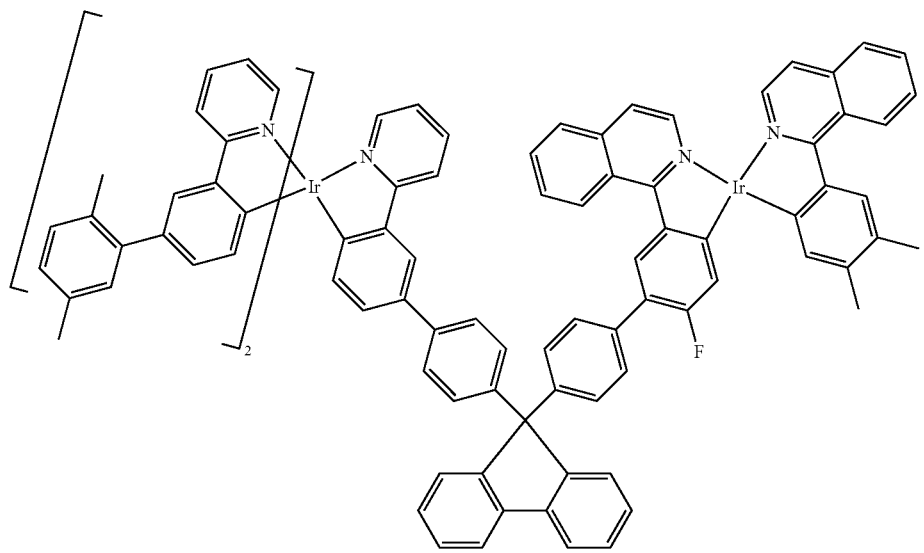
formula (77)
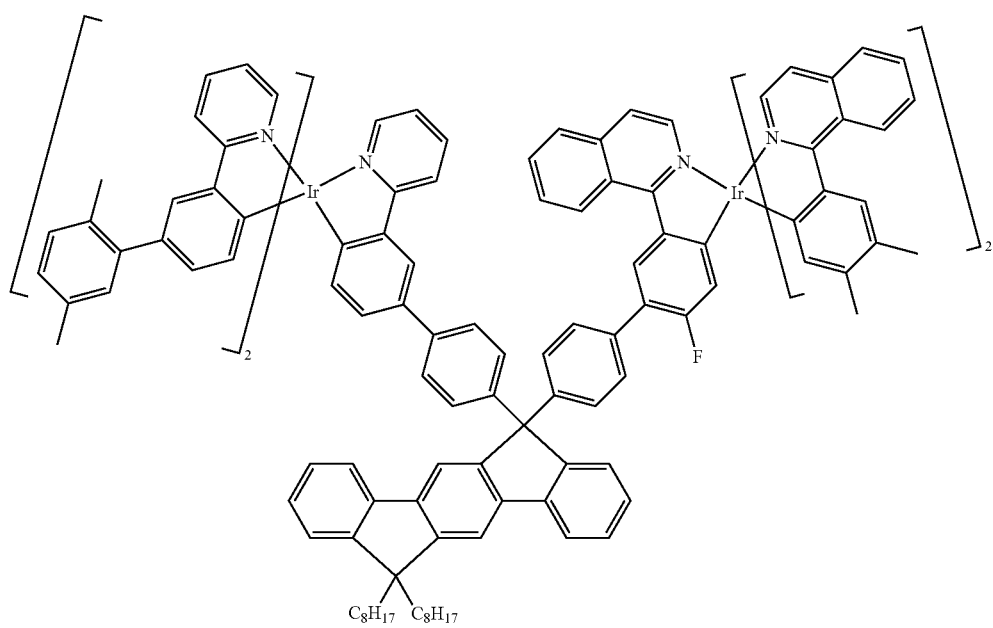
formula (78)
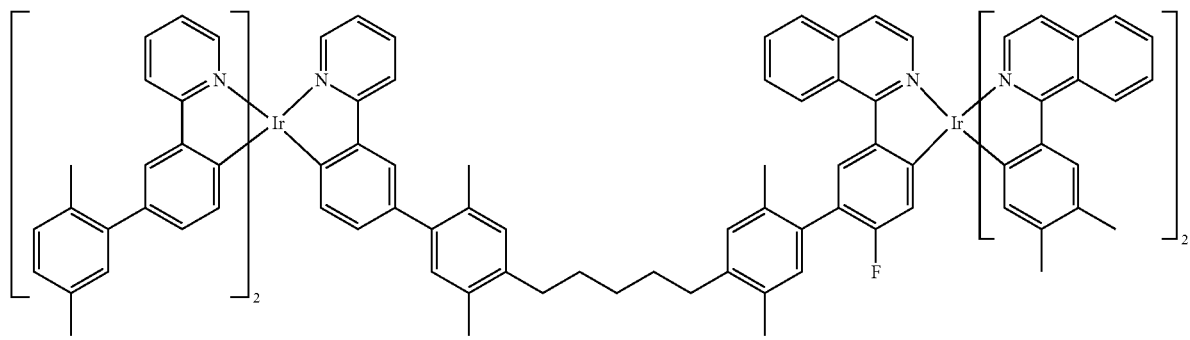

formula (79)
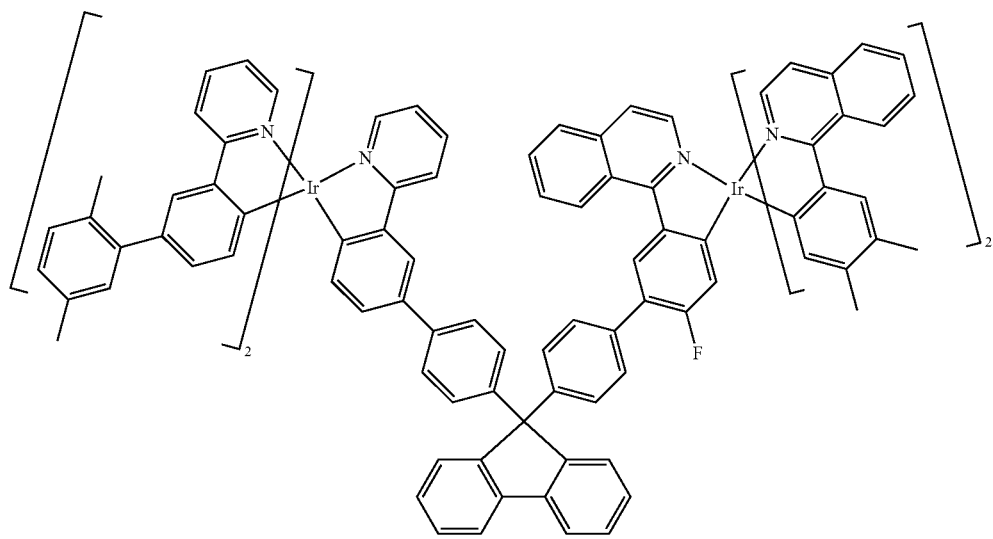
formula (80)
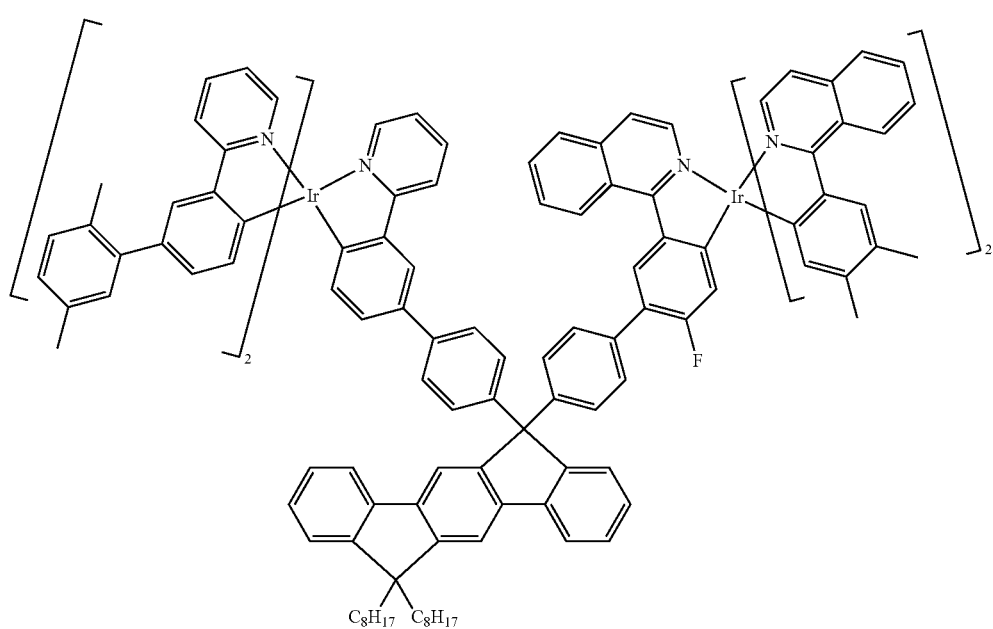
formula (81)
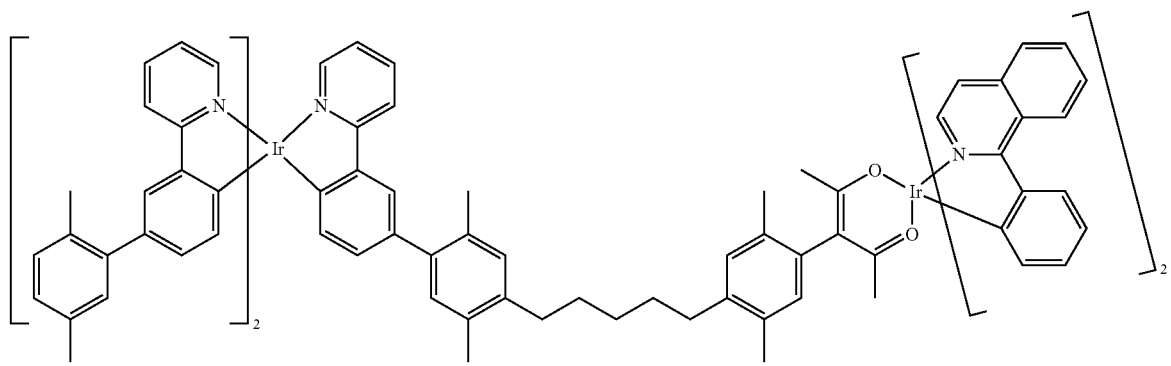

-continued
formula (82)
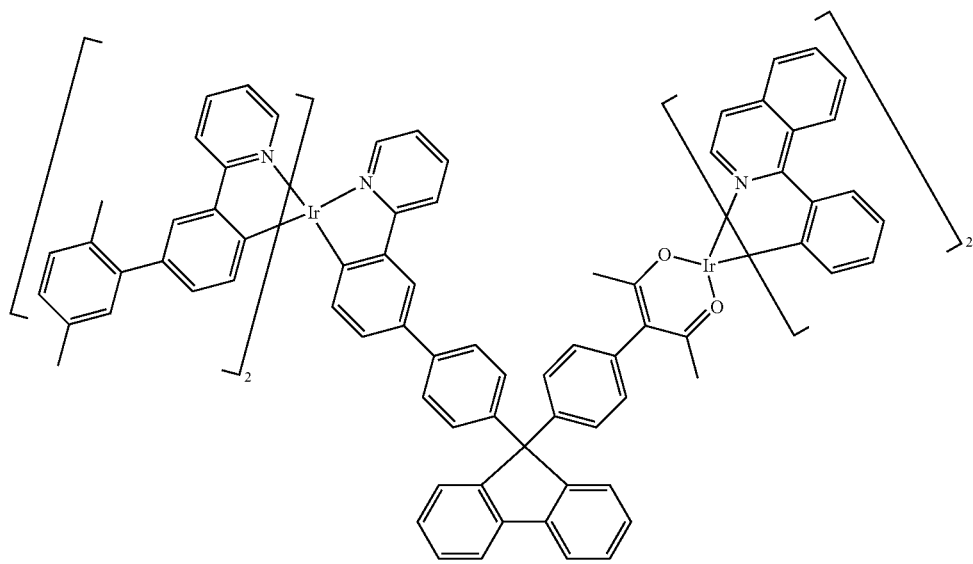
formula (83)
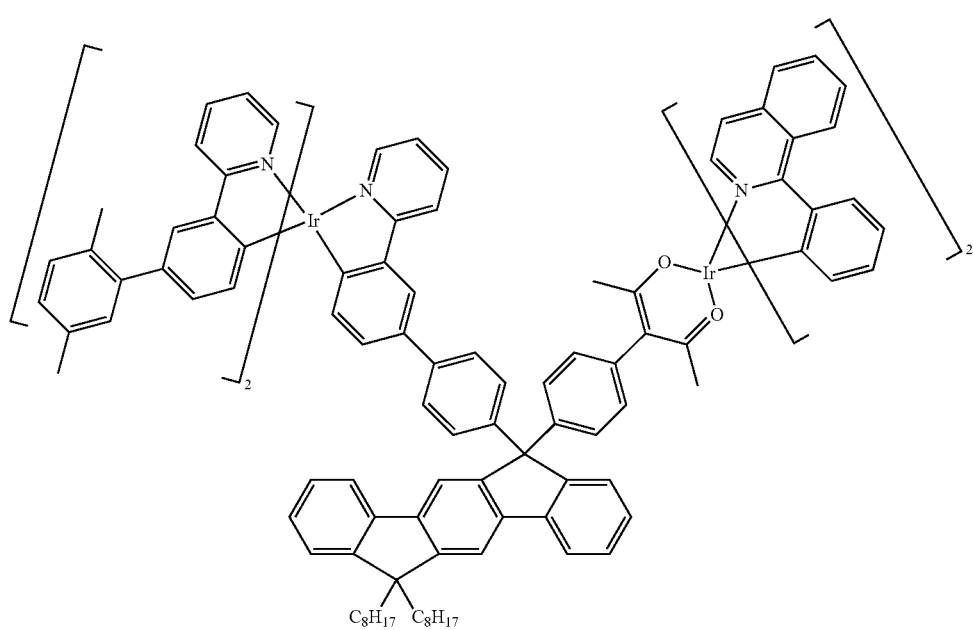
formula (84)
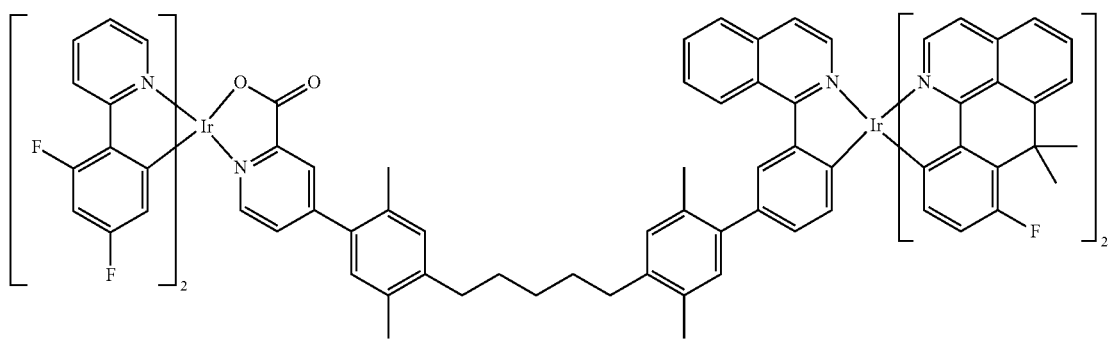

formula (85)
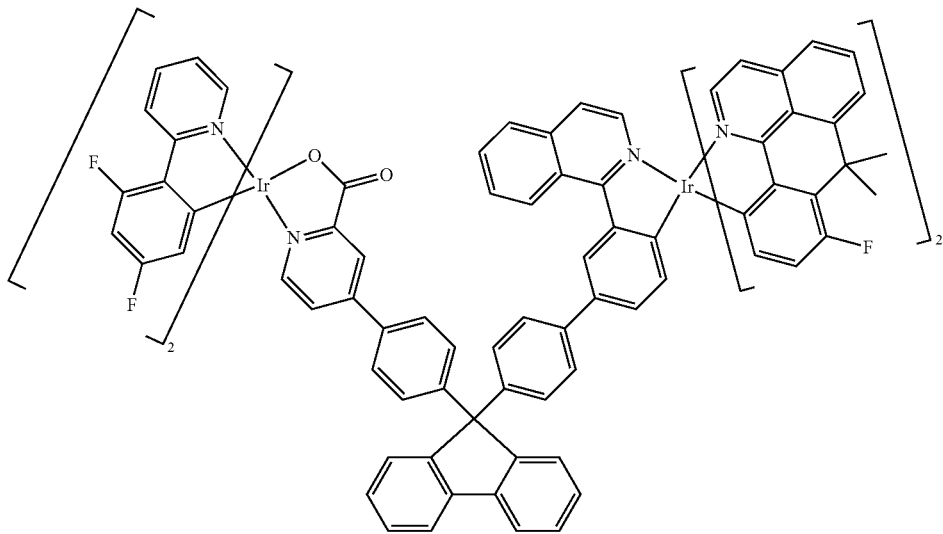
formula (86)
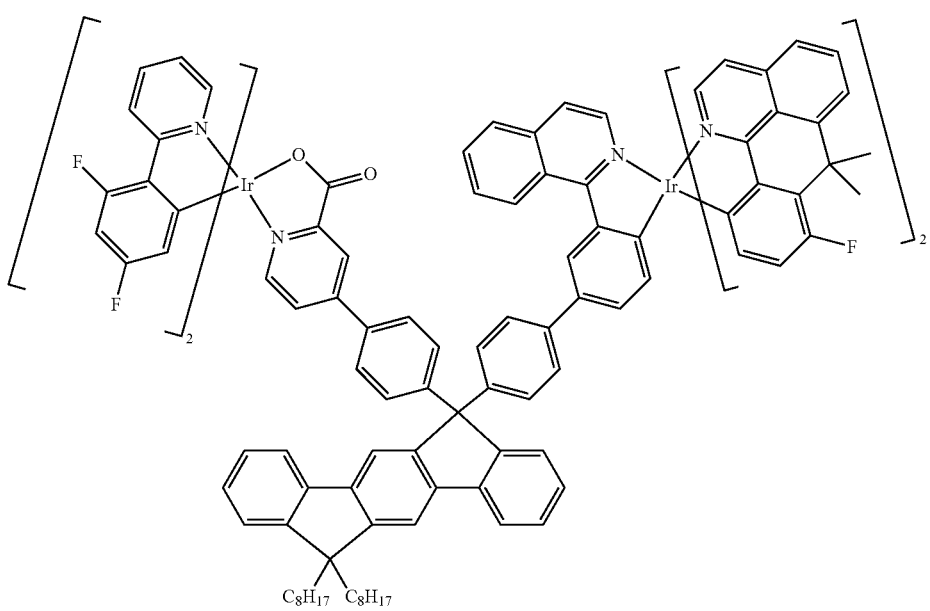
formula (87)
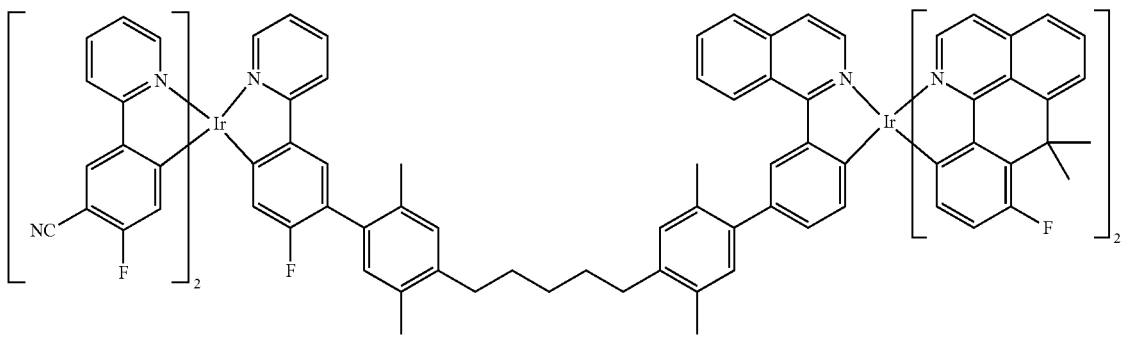

formula (88)
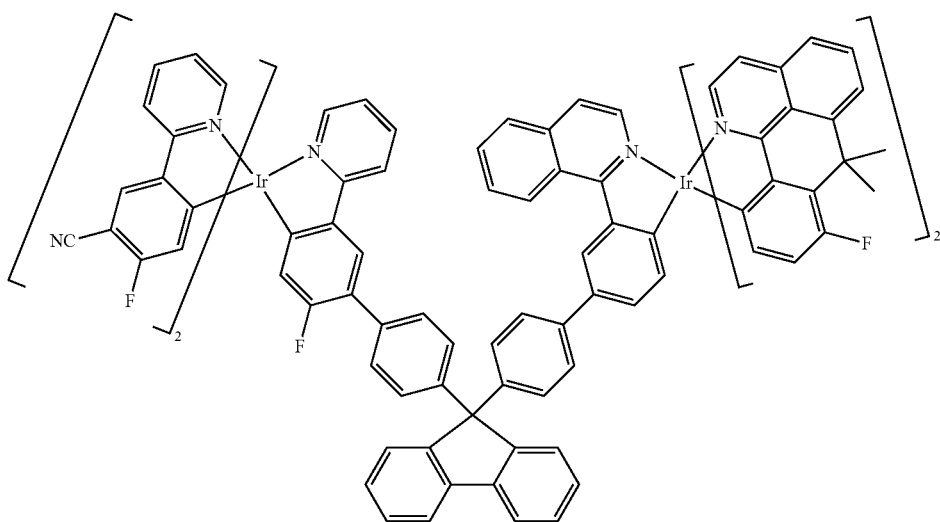
formula (89)
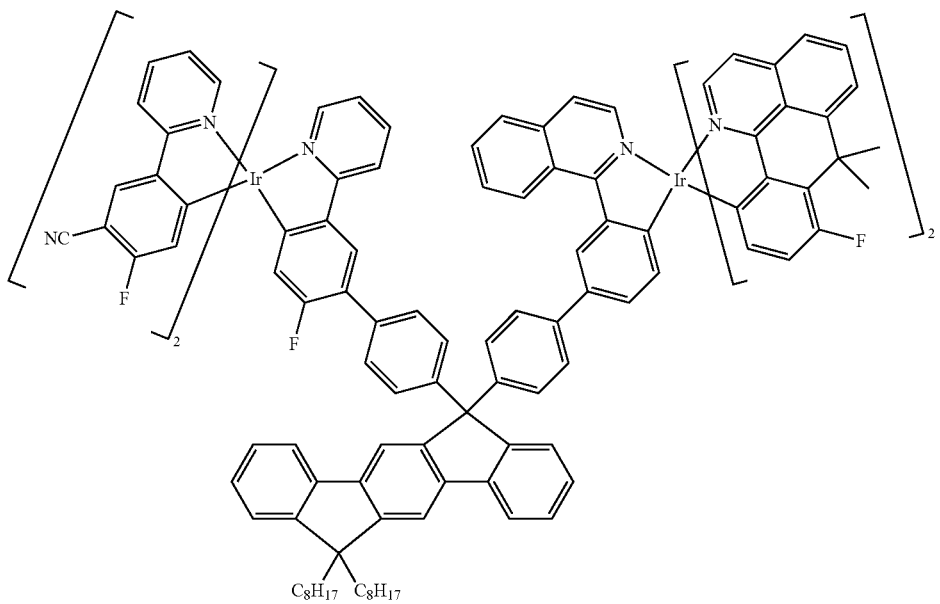
formula (90)
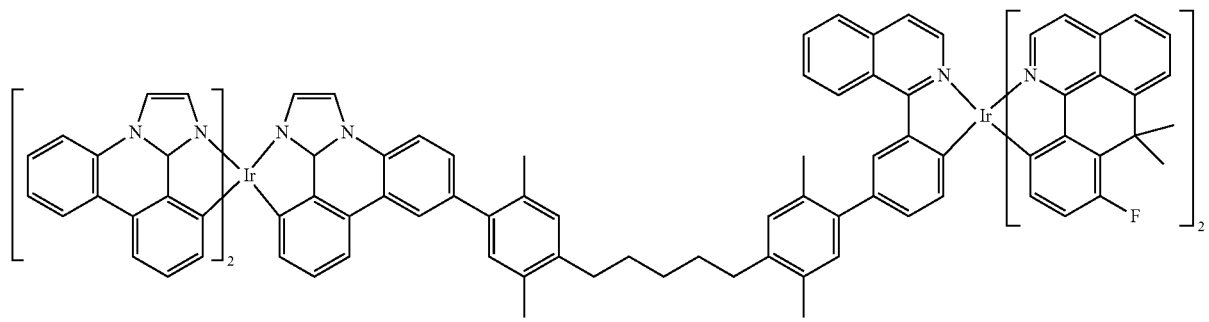

formula (91)
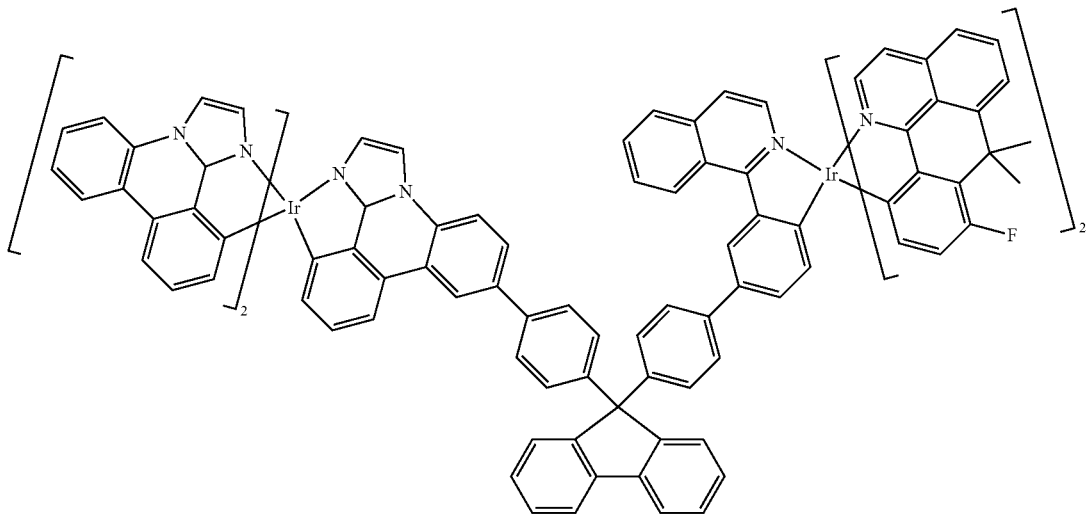
formula (92)
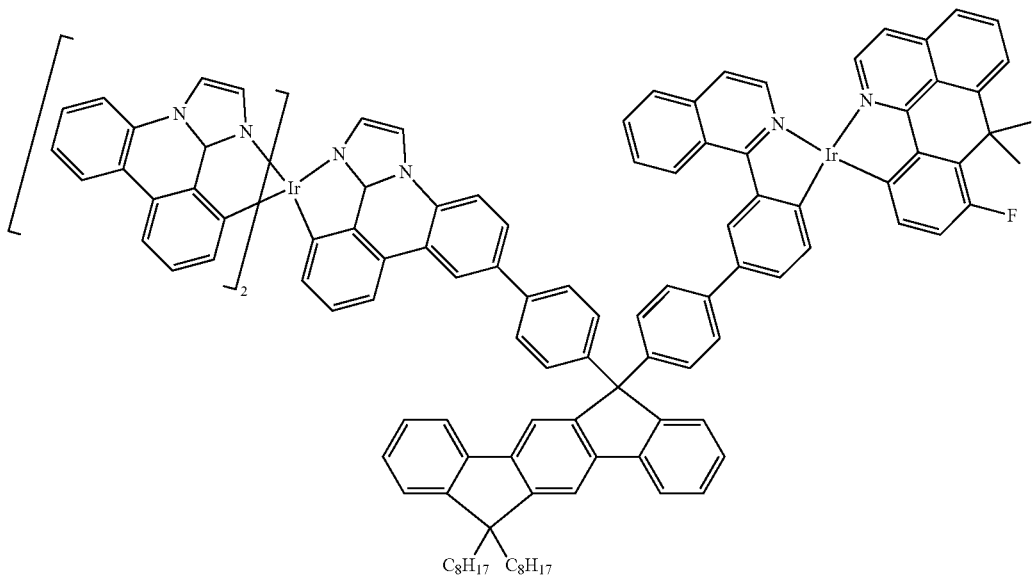
formula (93)
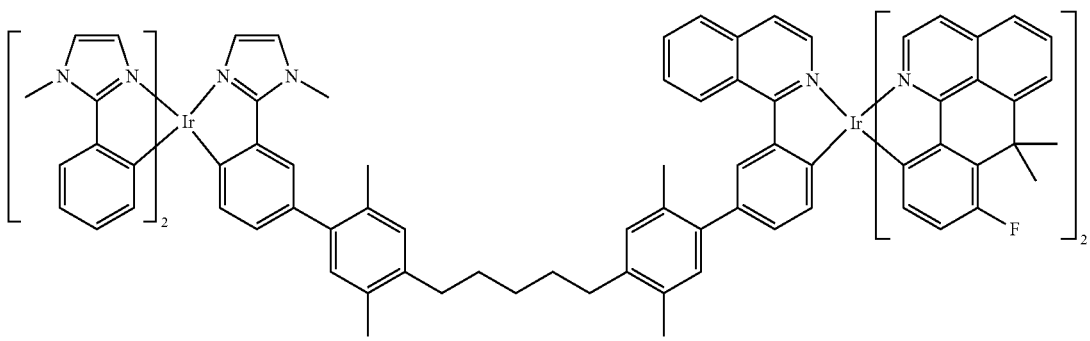

formula (94)
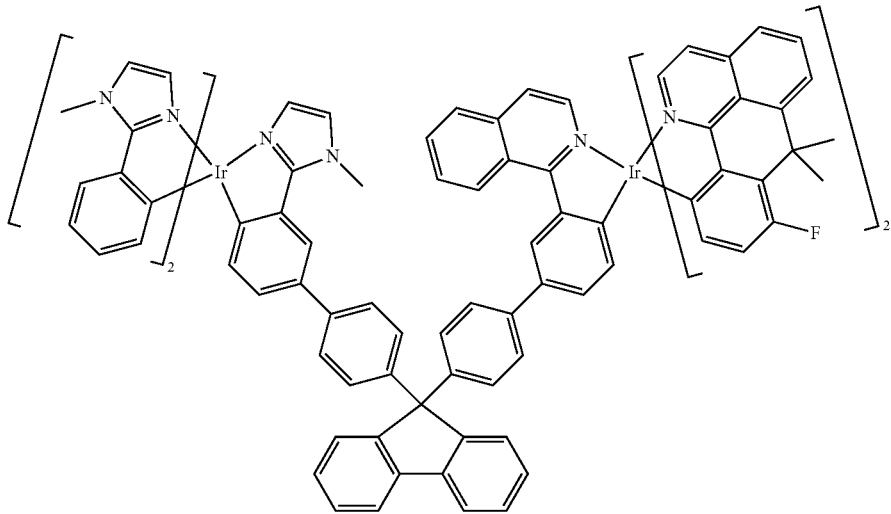
formula (95)
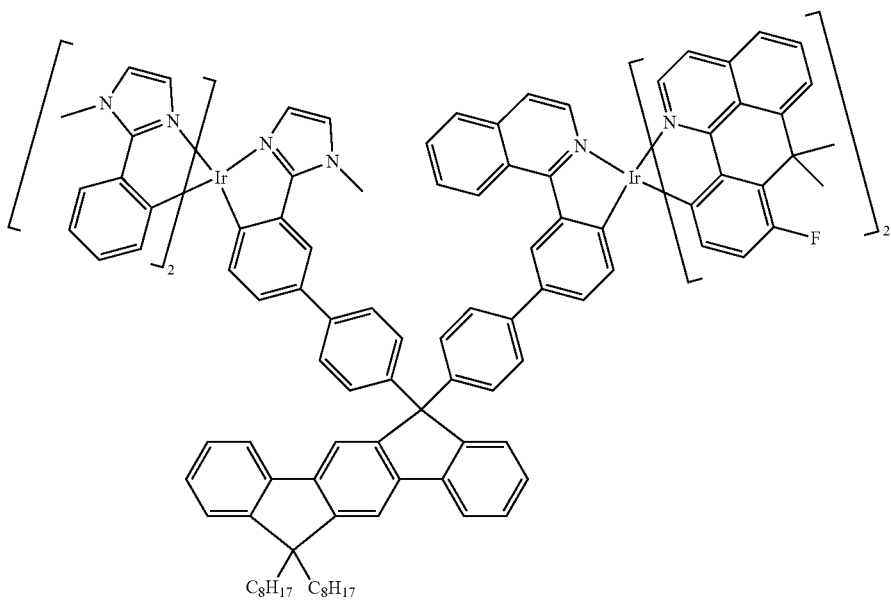
formula (96)
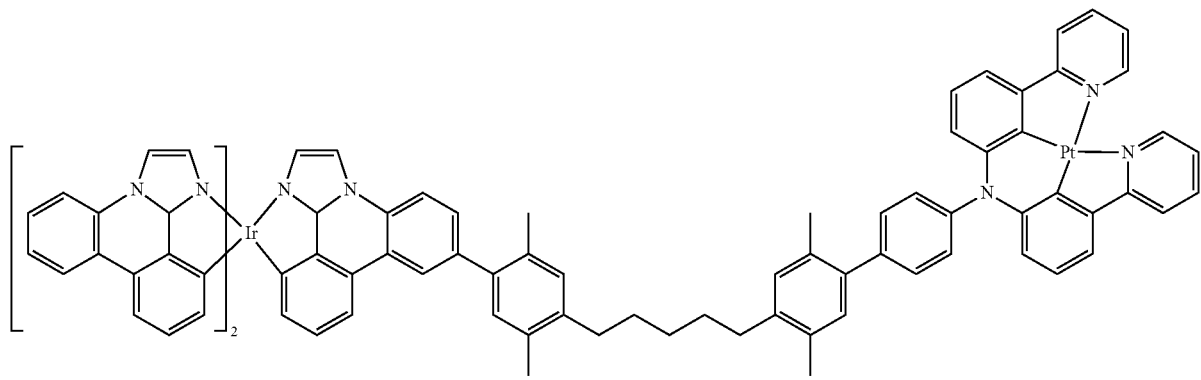

formula (97)
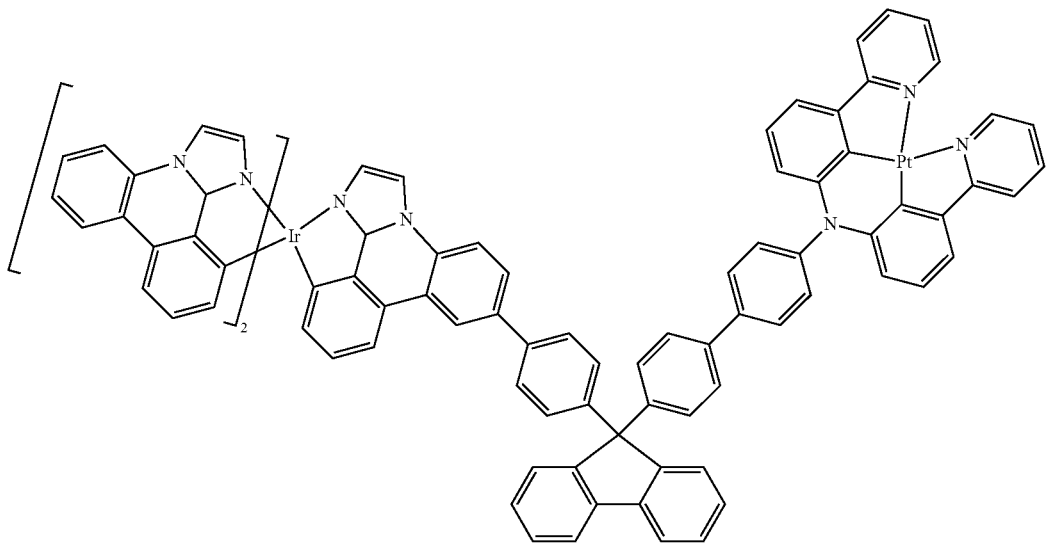
formula (98)
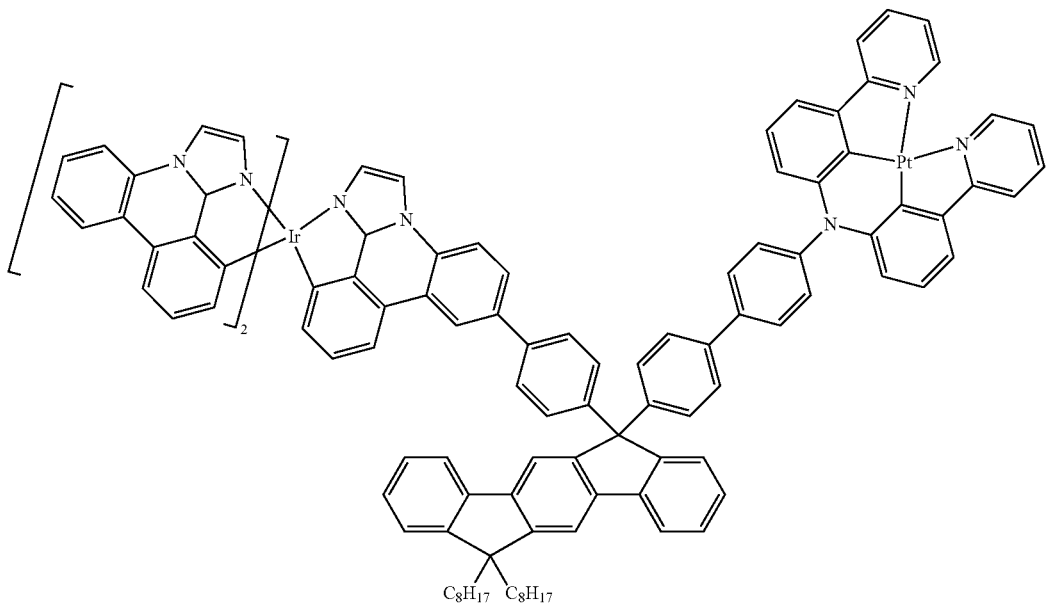
formula (99)
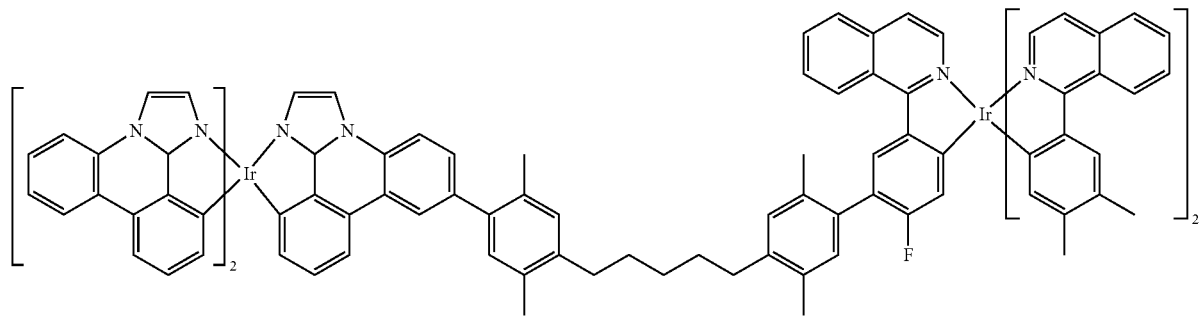

formula (100)
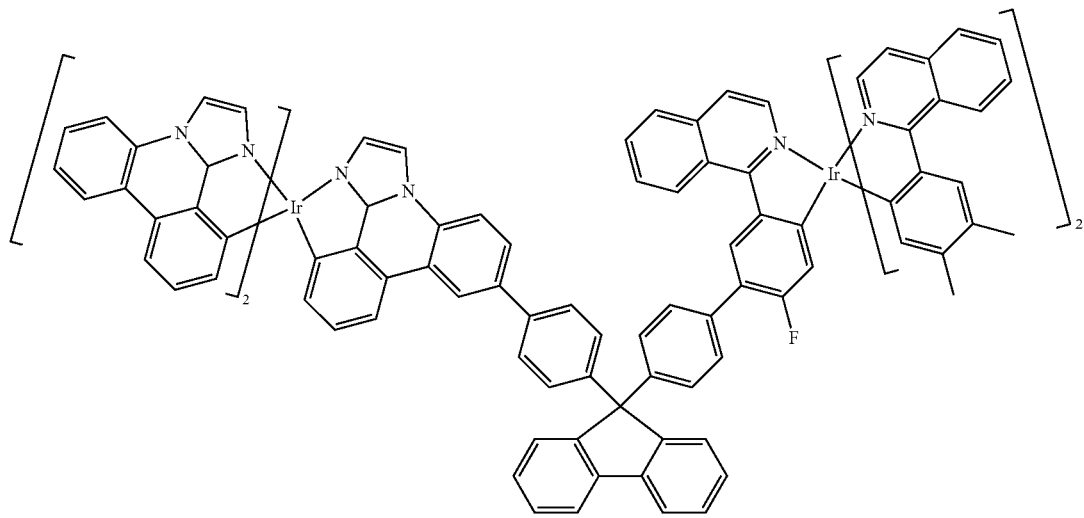
formula (101)
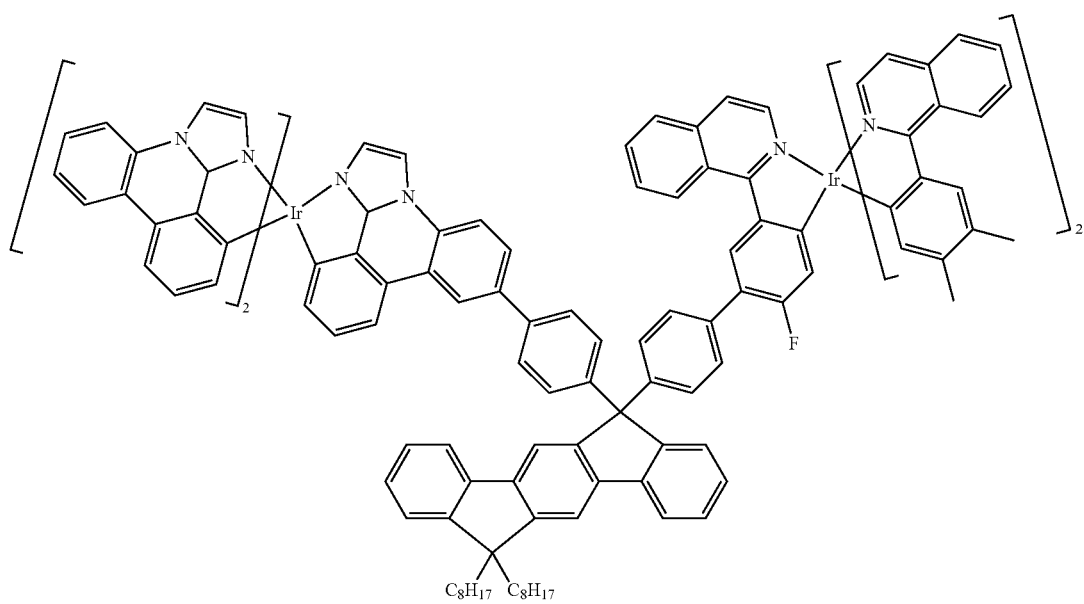
formula (102)
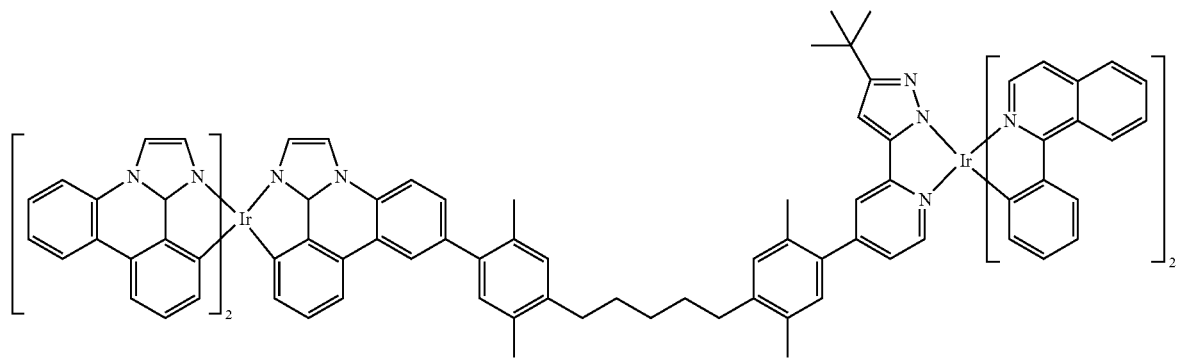

formula (103)
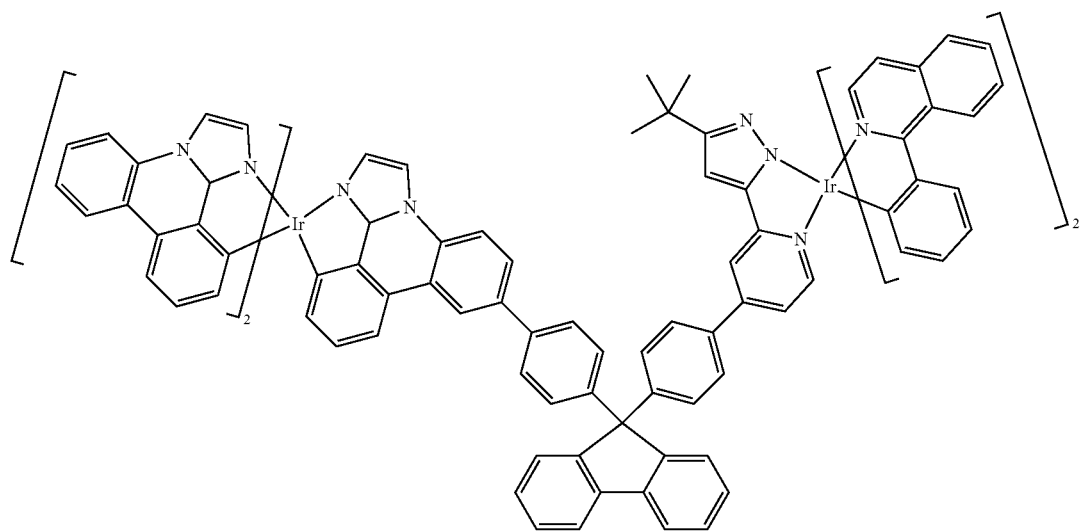
formula (104)
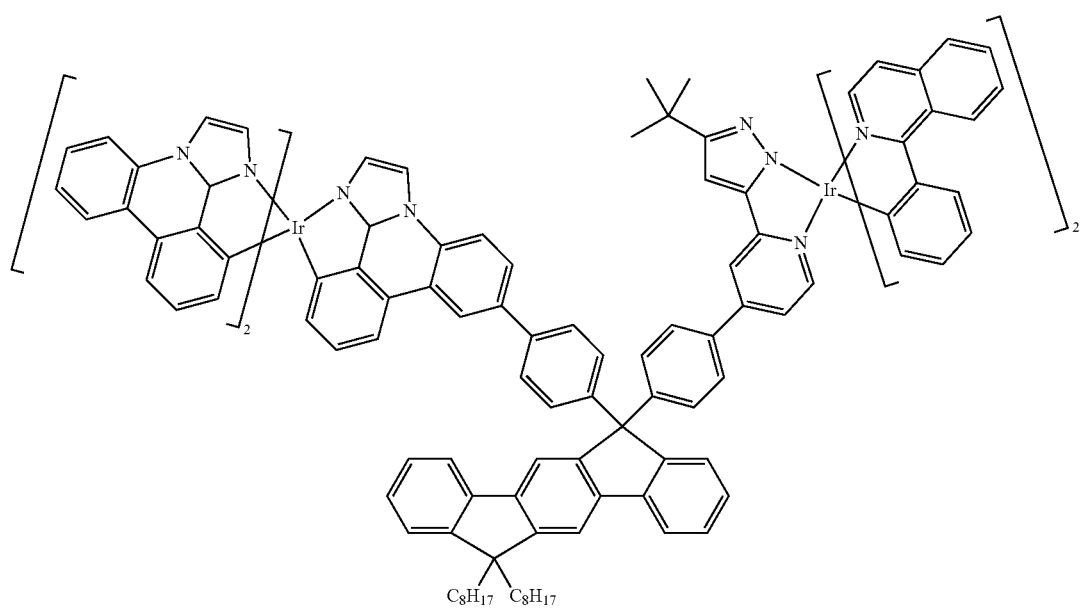
formula (105)
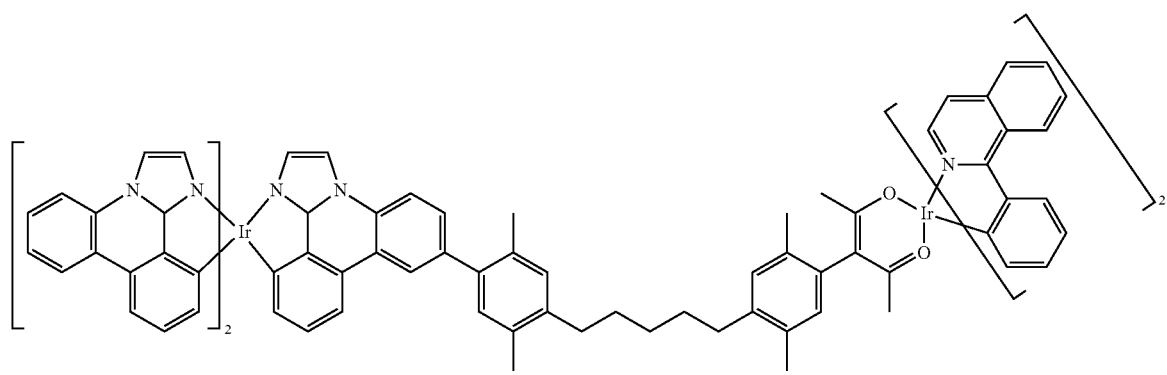

formula (106)
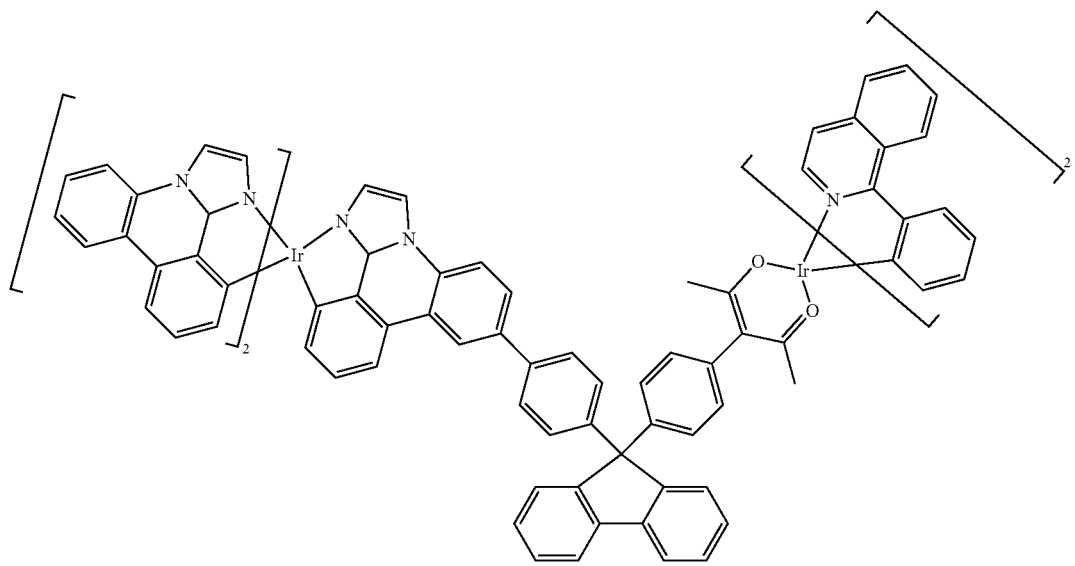
formula (107)
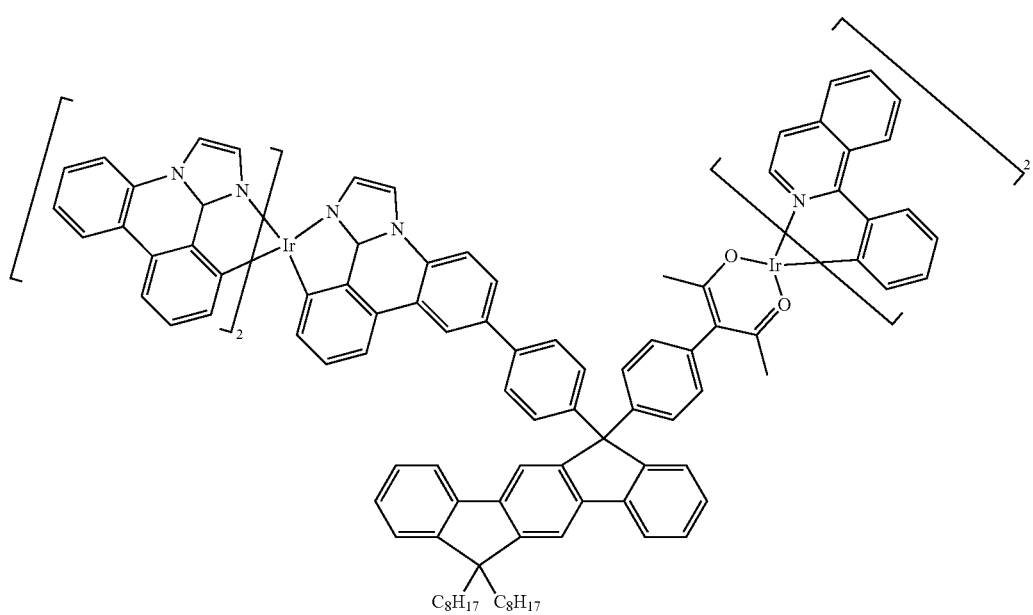
formula (108)
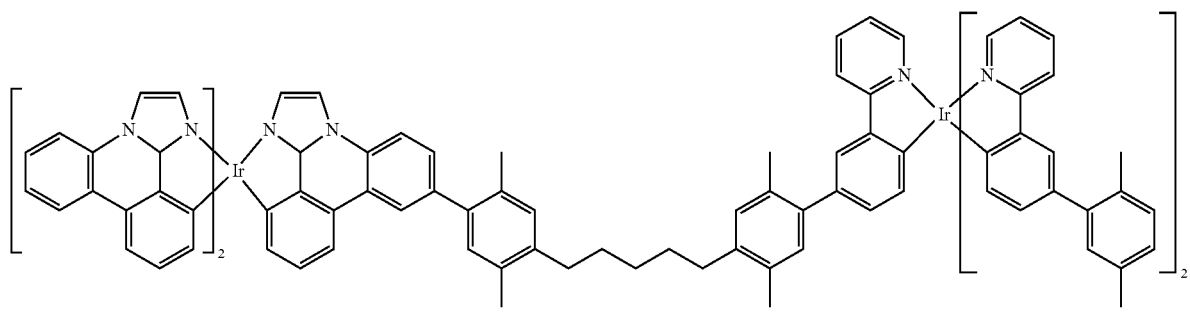

formula (109)
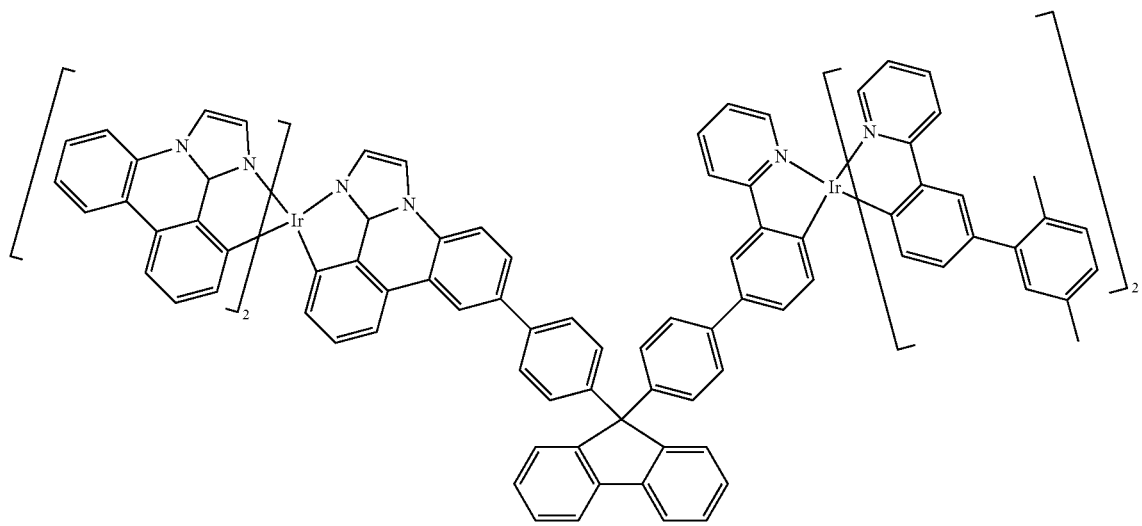
formula (110)
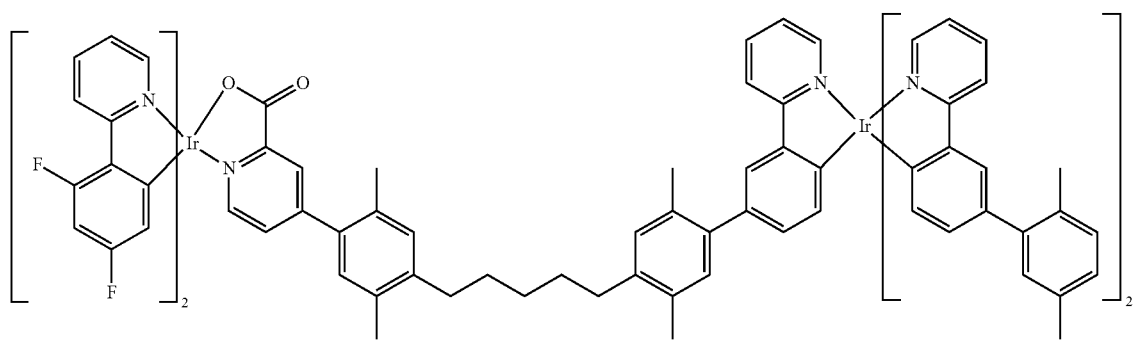
formula (111)
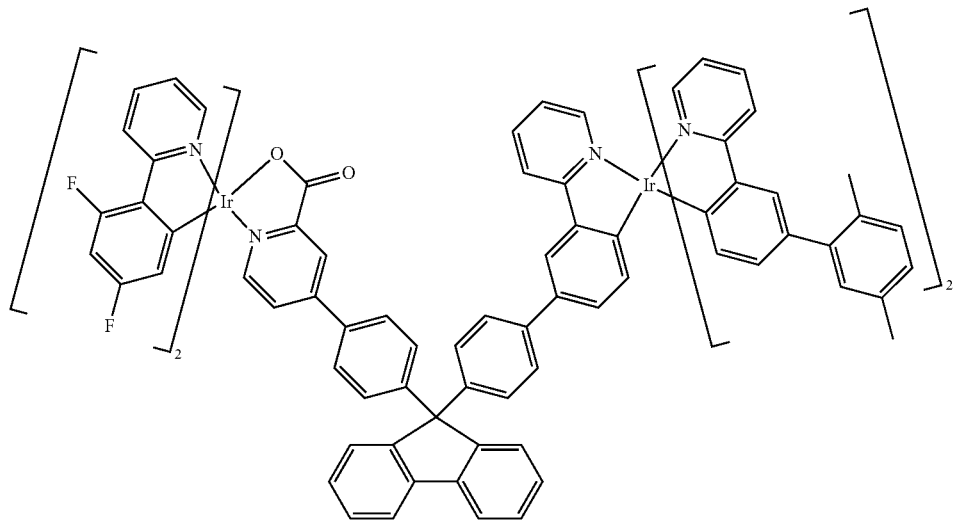

formula (112)
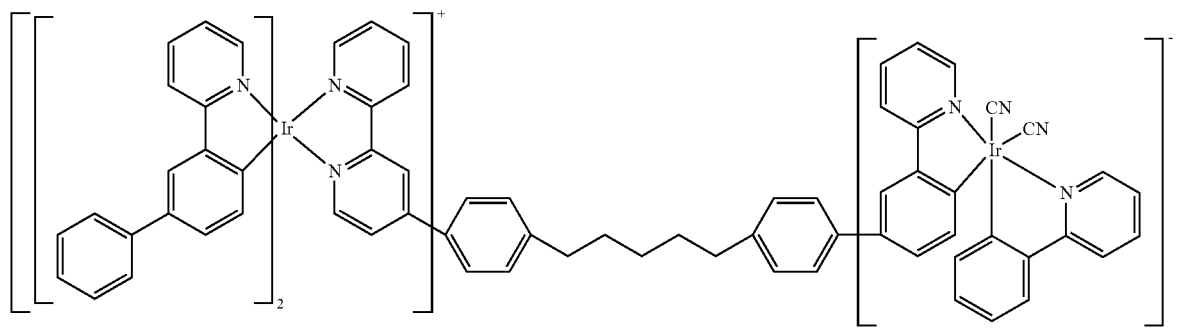
formula (113)
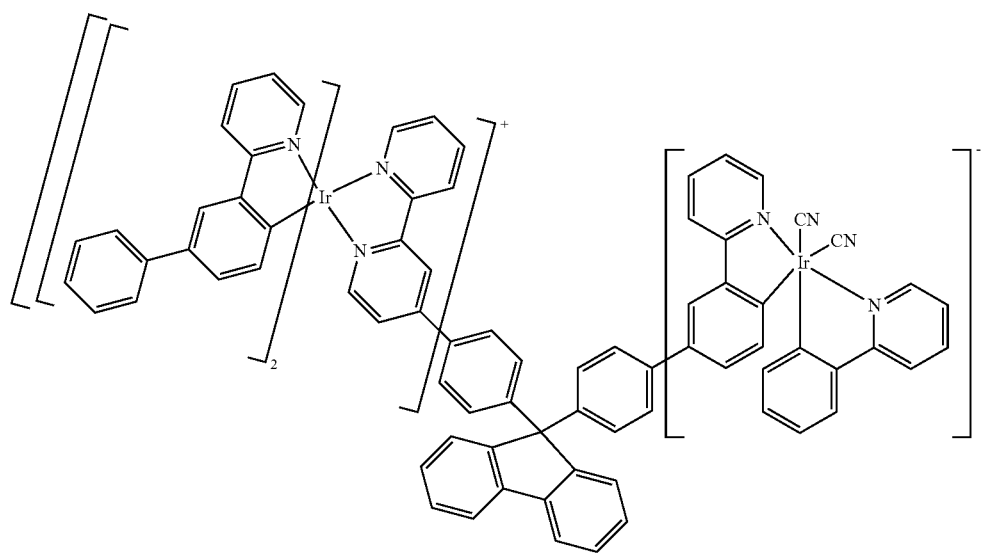
formula (114)
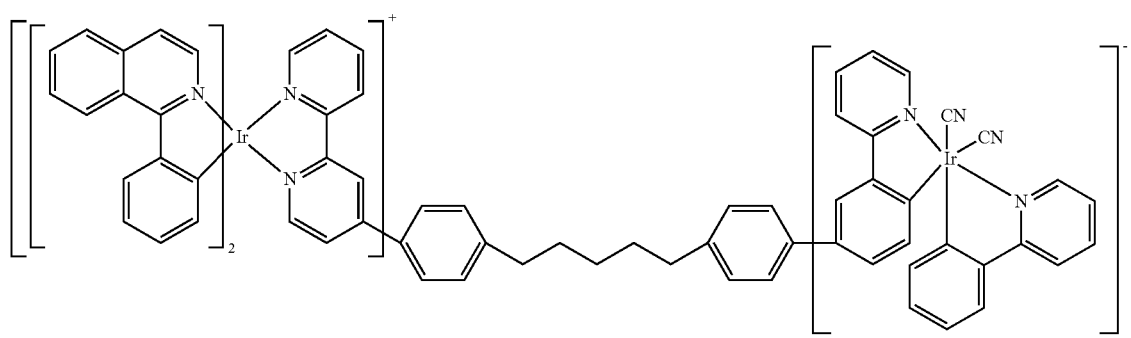

formula (115)

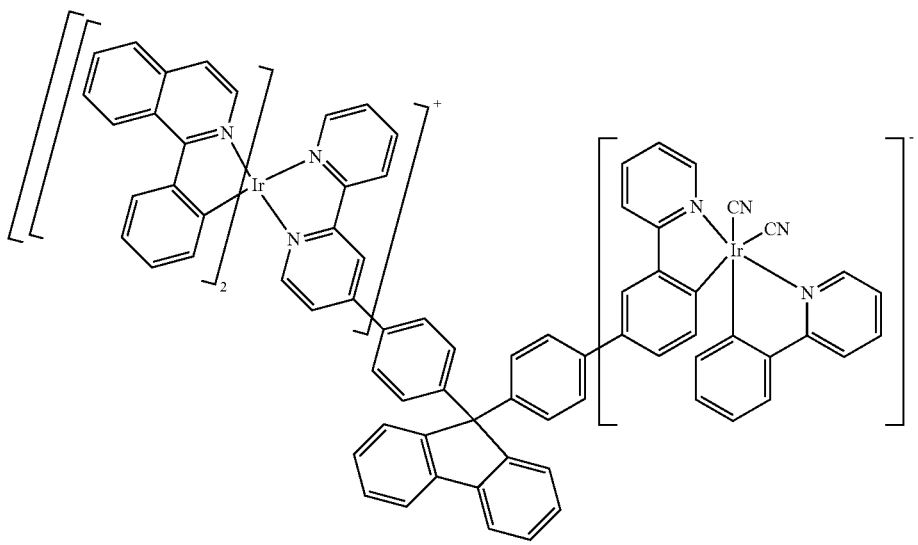

The compounds of the formulae (84) to (107) are compounds in which one of the metal-ligand coordination compound units phosphoresces in the wavelength range of blue light and the other phosphoresces in the wavelength range of red light.

The compounds of the formulae (108) to (111) are compounds in which one of the metal-ligand coordination compound units phosphoresces in the wavelength range of blue light and the other phosphoresces in the wavelength range of red light.

A "$C_{1-40}$-alkyl" in the present invention is preferably taken to mean linear, branched or cyclic alkyl groups. The linear alkyl groups preferably have 1 to 6, 1 to 10 or 1 to 40 carbon atoms. The branched or cyclic alkyl groups preferably have 3 to 6, 3 to 10 or 3 to 40 carbon atoms. Preference is given to alkyl groups having 1 to 6, or 3 to 6 carbon atoms, particularly preferably 1 to 3, or 3 carbon atoms. One or more hydrogen atoms on these alkyl groups may be replaced by a fluorine atom. In addition, one or more of the $CH_2$ groups in these units may be replaced by NR, O or S (R here is a radical selected from the group consisting of H and $C_{1-6}$-alkyl). If one or more of the $CH_2$ groups is replaced by NR, O or S, it is particularly preferred for only one of these groups to be replaced; particularly preferably by an O atom. Examples of such compounds include the following: methyl, ethyl, n-propyl, i-propyl, n-butyl, i-butyl, s-butyl, t-butyl, 2-methylbutyl, n-pentyl, s-pentyl, n-hexyl, n-heptyl, n-octyl, 2-ethylhexyl, trifluoromethyl, pentafluoroethyl, 2,2,2-trifluoroethyl, cyclopentyl, cyclohexyl, cycloheptyl and cyclooctyl.

A "$C_{2-40}$-alkenyl" is taken to mean a linear alkenyl group having 2 to 40 carbon atoms or a branched or cyclic alkenyl group having 3 to 40 carbon atoms. It is more preferably a group having 2 or 3 to 20, even more preferably a group having 2 or 3 to 10 and most preferably a group having 2 or 3 to 6 carbon atoms. One or more hydrogen atoms may be replaced by a fluorine atom. In addition, one or more of the $CH_2$ groups in these units may be replaced by NR, O or S (R here is a radical selected from the group consisting of H and $C_{1-6}$-alkyl). If one or more of the $CH_2$ groups is replaced by NR, O or S, it is particularly preferred for only one of these groups to be replaced. Examples thereof which may be mentioned are ethenyl, propenyl, butenyl, pentenyl, cyclopentenyl, hexenyl, cyclohexenyl, heptenyl, cycloheptenyl, octenyl and cyclooctenyl.

A "$C_{2-40}$-alkynyl" is taken to mean a linear or branched alkynyl group having 2 to 40 carbon atoms. The alkynyl group more preferably has 2 to 20, even more preferably 2 to 10 and most preferably 2 to 6 carbon atoms. One or more hydrogen atoms may be replaced by a fluorine atom. In addition, one or more of the $CH_2$ groups in these units may be replaced by NR, O or S (R here is a radical selected from the group consisting of H and $C_{1-6}$-alkyl). If one or more of the $CH_2$ groups is replaced by NR, O or S, it is particularly preferred for only one of these groups to be replaced. Examples thereof which may be mentioned are ethynyl, propynyl, butynyl, pentynyl, hexynyl and octynyl.

"$C_{1-12}$-alkylene" in the present invention is taken to mean a linear or branched alkyl group as defined above, preferably having 1 to 12, more preferably 1 to 6 and most preferably 1 to 3 carbon atoms, in which a hydrogen radical is not present and a further bond is present at this site.

"$C_{3-8}$-cycloalkylene" in the present invention is taken to mean a cyclic alkyl group as defined above, preferably having 3 to 8, more preferably 5 to 8 and most preferably 5 or 6 carbon atoms, in which a hydrogen radical is not present and a further bond is present at this site.

"Mono($C_{1-12}$-alkyl)silylene" in the present invention is taken to mean an ($SiH_3$), ($SiH_2$) or (SiH) unit which is linked to a linear or branched alkyl group (as defined above) having 1 or 3 to 12 carbon atoms, more preferably 1 or 3 to 6 carbon atoms. This group is a divalent unit, which can bond via a C atom of an alkyl group and via the Si atom (then $SiH_2$ unit) or via two C atoms of one or two alkyl groups (then $SiH_3$ unit) or both times via the Si atom (then SiH unit). The examples indicated above in compound "$C_{1-40}$-alkyl" also apply here to the alkyl group present.

"Di($C_{1-12}$-alkyl)silylene" in the present invention is taken to mean an ($SiH_2$), (SiH) or (Si) unit which is linked to two linear or branched alkyl groups (as defined above) having 1 or 3 to 12 carbon atoms, more preferably 1 or 3 to 6 carbon atoms, which are identical or different on each occurrence. This group is a divalent unit, which can bond via a C atom of an alkyl group and via the Si atom (then SiH unit) or via two C atoms of one or two alkyl groups (then SiH$_2$ unit) or both times via the Si atom (then Si unit). The examples indicated above in compound "C$_{1-40}$-alkyl" also apply here to the alkyl groups present.

"Tri(C$_{1-12}$-alkyl)silylene" in the present invention is taken to mean an (SiH) or (Si) unit which is linked to three linear or branched alkyl groups (as defined above) having 1 or 3 to 12 carbon atoms, more preferably 1 or 3 to 6 carbon atoms, which are identical or different on each occurrence. This group is a divalent unit, which can bond via a C atom of an alkyl group and via the Si atom (then Si unit) or via two C atoms of one or two alkyl groups (then SiH unit). The examples indicated above in connection with the definition of "C$_{1-40}$-alkyl" also apply here to the alkyl groups present.

A silylene group which is substituted by one, two or three mono- or polycyclic aromatic or heteroaromatic ring systems having 5 to 60 aromatic ring atoms is taken to mean an Si$_1$-silyl group which is substituted by one, two or three mono- or polycyclic aromatic or heteroaromatic ring systems having 5 to 60 aromatic ring atoms. This group is a divalent group, which can bond either twice via the Si atom or once via the Si atom and once via a ring atom of the ring system or both times via ring atoms of the ring system.

"Si$_{1-5}$-silylene" in the present compound is taken to mean a silyl group having 1 or 3 to 5 silicon atoms, which is linear or branched. It is a divalent unit which bonds via the same or different Si atoms. Examples thereof are monosilyl, disilyl, trisilyl, tetrasilyl and pentasilyl.

"C$_{1-12}$-alkyloxy-C$_{1-12}$-alkylene" in the present invention is taken to mean a divalent ether unit having two linear or branched alkyl groups having 1 or 3 to 12, more preferably 1 or 3 to 6 carbon atoms, which are bonded via an oxygen atom. The examples indicated above in connection with the definition of "C$_{1-40}$-alkyl" also apply here to the alkyl groups present. The unit is a divalent unit, which can bond either via one or two C atoms of the same alkyl group or via two C atoms of different alkyl groups.

"C$_{1-12}$-alkylthio-C$_{1-12}$-alkylene" in the present invention is taken to mean a divalent thioether unit having two linear or branched alkyl groups having 1 or 3 to 12, more preferably 1 or 3 to 6 carbon atoms which are bonded via a sulfur atom. The examples indicated above in connection with the definition of "C$_{1-40}$-alkyl" also apply here to the alkyl groups present. The unit is a divalent unit, which can bond either via one or two C atoms of the same alkyl group or via two C atoms of different alkyl groups.

"Aryl-C$_{1-12}$-alkyloxy-C$_{1-12}$-alkylene" in the present invention is taken to mean a divalent unit as defined above for "C$_{1-12}$-alkyloxy-C$_{1-12}$-alkylene", where an alkyl group is substituted by an aryl which represents a mono- or polycyclic aromatic or heteroaromatic ring system having 5 to 60 aromatic ring atoms as defined below.

"Sulfone" in the present application is taken to mean a divalent —S(=O)$_2$-unit.

"C$_{1-12}$-alkylenesulfone" in the present invention is an —S(=O)$_2$— unit which is substituted by an alkylene group having 1 to 12 carbon atoms. It is a divalent unit, which can bond via a C atom of the alkylene group and via the S atom. The disclosure made above in connection with the definition of "C$_{1-12}$-alkylene" also applies to the alkylene groups which are preferred here.

"Sulfoxide" in the present invention is taken to mean a divalent —S(=O)— unit.

"C$_{1-12}$-alkylene sulfoxide" in the present invention is an —S(=O)— unit which is substituted by an alkylene group having 1 to 12 carbon atoms. It is a divalent unit, which can bond via a C atom of the alkylene group and via the S atom.

The disclosure made above in connection with the definition of "C$_{1-12}$-alkylene" also applies to the alkylene groups which are preferred here.

A mono- or polycyclic aromatic or heteroaromatic hydrocarbon radical preferably contains 5 to 20, more preferably 5 to 10, most preferably 5 or 6 aromatic ring atoms. If the unit is an aromatic unit, it preferably contains 6 to 20, more preferably 6 to 10, most preferably 6 carbon atoms as ring atoms. If the unit is a heteroaromatic unit, it contains 5 to 20, more preferably 5 to 10, most preferably 5 aromatic ring atoms, at least one of which is a heteroatom. The heteroatoms are preferably selected from N, O and/or S. An aromatic or heteroaromatic unit here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran and indole, etc.

Examples according to the invention of the aromatic or heteroaromatic hydrocarbon radicals are accordingly: benzene, naphthalene, anthracene, phenanthrene, pyrene, chrysene, benzanthracene, perylene, naphthacene, pentacene, benzopyrene, furan, benzofuran, isobenzofuran, dibenzofuran, thiophene, benzothiophene, isobenzothiophene, dibenzothiophene, pyrrole, indole, isoindole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A mono- or polycyclic aromatic or heteroaromatic unit having 5 to 60 aromatic ring atoms is preferably taken to mean a mono- or polycyclic aromatic or heteroaromatic hydrocarbon radical as defined above having 5 to 60 aromatic ring atoms, in which one or more H atoms are not present and a bond to a further unit or radical is present at this site, so that it represents a di-, tri-, tetra- or polyvalent unit.

A mono- or polycyclic aromatic ring system in the sense of this invention is preferably taken to mean an aromatic ring system having 6 to 60 carbon atoms, preferably 6 to 30, particularly preferably 6 to 10 carbon atoms. An aromatic ring system in the sense of the present invention is intended to be taken to mean a system which does not necessarily contain only aromatic groups, but instead in which, in addition, a plurality of aromatic may be interrupted by a short non-aromatic unit (<10% of the atoms other than H, preferably <5% of the atoms other than H), such as, for example, sp$^3$-hybridised C, O, N, etc. These aromatic ring systems may be monocyclic or polycyclic, i.e. they may contain one ring (for example phenyl) or two or more rings, which may also be condensed (for example naphthyl) or covalently linked (for example biphenyl), or contain a combination of condensed and linked rings.

Preferred aromatic ring systems are, for example, phenyl, biphenyl, triphenyl, naphthyl, anthracyl, binaphthyl, phenanthryl, dihydrophenanthryl, pyrene, dihydropyrene, chrysene, perylene, tetracene, pentacene, benzopyrene, fluorene and indene.

A mono- or polycyclic heteroaromatic ring system in the sense of this invention is preferably taken to mean a heteroaromatic ring system having 5 to 60 ring atoms, preferably 5 to 30, particularly preferably 5 to 14 ring atoms. The heteroaromatic ring system contains at least one heteroatom selected from N, O and S (remaining atoms are carbon). A heteroaromatic ring system is additionally intended to be taken to mean a system which does not necessarily contain only aromatic or heteroaromatic groups, but instead in which, in addition, a plurality of aromatic or heteroaromatic groups may be interrupted by a short non-aromatic unit (<10% of the atoms other than H, preferably <5% of the atoms other than H), such as, for example, $sp^3$-hybridised C, O, N, etc. These heteroaromatic ring systems may be monocyclic or polycyclic, i.e. they may contain one ring (for example pyridyl) or two or more rings, which may also be condensed or covalently linked, or contain a combination of condensed and linked rings.

Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene or combinations of these groups. Particular preference is given to imidazole, benzimidazole and pyridine.

The general terms "alkyl(ene)", "cycloalkyl(ene)", "alkylsilyl(ene)", "arylsilyl(ene)", "alkylalkoxyalkyl(ene)", "arylalkoxyalkyl(ene)", "alkylthioalkyl(ene)", "alkylene sulfone", "alkylene sulfoxide" are taken to mean groups in which the aryl group is as defined above and the alkyl groups or alkylene groups each has, independently of one another, 1 to 12 C atoms, where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

The present invention furthermore relates to a multilayer structure which comprises a layer which comprises a compound of the formula (1) according to the invention.

A multilayer structure in the present invention is taken to mean a multilayer structure comprising two or more layers, which are preferably applied successively to a glass support.

The layers may comprise individual compounds according to the invention. It is preferred for the layers to comprise further compounds or polymers or oligomers having different properties.

The present invention furthermore relates to a formulation, in particular a solution, dispersion or emulsion, comprising at least one compound of the formula (1) according to the invention and at least one solvent. Solvents which can be employed are all conceivable ones which are capable of dissolving the compounds according to the invention or forming a suspension with them. The solvents are particularly preferably organic solvents. The following organic solvents are preferred in accordance with the invention here—without restricting the invention: dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 1,1,1-trichloroethane, 1,1,2,2-tetrachloroethane, ethyl acetate, n-butyl acetate, dimethylformamide, dimethylacetamide, dimethyl sulfoxide, tetralin, decalin, indane and/or mixtures thereof.

The concentration of the compound of the formula 1 according to the invention in the solution is preferably 0.1 to 10% by weight, more preferably 0.5 to 5% by weight, based on the total weight of the solution. The solution optionally also comprises one or more binders in order to adjust the rheological properties of the solution correspondingly, as described, for example, in WO 2005/055248 A1.

After appropriate mixing and ageing of the solutions, these are divided into one of the following categories: "full" solution, "borderline" solution or insoluble. The border line is drawn between these categories with reference to the solubility parameters. The corresponding values can be obtained from the literature, such as, for example, from "Crowley, J. D., Teague, G. S. Jr. and Lowe, J. W. Jr., Journal of Paint Technology, 38, No. 496, 296 (1966)".

Solvent mixtures can also be used and are identified as described in "Solvents, W. H. Ellis, Federation of Societies for Coatings Technology, pp. 9 to 10, 1986". Processes of this type can result in a mixture of so-called "non"-solvents which dissolve the composition, although it is desirable to have at least one true solvent in the mixture.

A further preferred form of the formulation is an emulsion, and more preferably a miniemulsion, which are prepared, in particular, as heterophase systems, in which stable nanodroplets of a first phase are dispersed in a second continuous phase. The present invention relates, in particular, to a miniemulsion in which the various components of the compound according to the invention are either arranged in the same phase or in different phases. Preferred distributions are the following:

1) The majority of all compounds according to the invention and the majority of all functional compounds are located in the continuous phase;
2) The majority of all compounds according to the invention is located in nanodroplets and the majority of all further functional compounds, such as, for example, the host compound, is located in the continuous phase.

Both a miniemulsion, in which the continuous phase is a polar phase, and also an inverse miniemulsion, in which the continuous phase is a non-polar phase, can be used in the present invention. The preferred form is a miniemulsion. In order to increase the kinetic stability of the emulsion, surfactants can also be admixed. The choice of the solvents for two-phase systems, the surfactants and the processing to give a stable miniemulsion should be known to a person skilled in the art in this area on the basis of his expert knowledge or through numerous publications, such as, for example, a comprehensive article by Landfester in Annu. Rev. Mater. Res. (06), 36, p. 231.

For use of so-called thin layers in electronic or opto-electronic devices, the compound according to the invention or a formulation thereof can be deposited by a correspondingly suitable process. Liquid coating of devices, such as, for example, of OLEDs, is more desirable than vacuum deposition techniques. Deposition methods from solution are particularly preferred. Preferred deposition techniques include, without correspondingly restricting the invention, dip coating, spin coating, ink-jet printing, letterpress printing, screen printing, doctor blaid coating, roller printing, reverse roller printing, offset lithography, flexographic printing, web printing, spray coating, brush coating or pad printing and slot-die coating. Ink-jet printing is particularly preferred and enables the production of high-resolution displays.

The solutions according to the invention can be applied to prefabricated device substrates with the aid of ink-jet printing or by microdispensing. To this end, preference is given to the use of industrial piezoelectric print heads, such as from Aprion, Hitachie-Koki, Inkjet Technology, On Target Technology, Picojet, Spectra, Trident, Xaar, in order to apply the organic semiconductor layers to a substrate. In addition, semi-industrial print heads, such as those from Brother, Epson, Konika, Seiko Instruments, Toshiba TEC or single-nozzle microdispensing equipment, as manufactured, for example, by Mikrodrop and Mikrofab, can also be used.

In order that the compound according to the invention can be applied by ink-jet printing or microdispensing, it should first be dissolved in a suitable solvent. The solvents must meet the above-mentioned requirements and must not have any disadvantageous effects on the print head selected. In addition, the solvents should have a boiling point of above 100° C., preferably above 140° C. and more preferably above 150° C., in order to avoid processing problems caused by drying-out of the solution inside the print head. Besides the above-mentioned solvents, the following solvents are also suitable: substituted and unsubstituted xylene derivatives, di-$C_{1-2}$-alkylformamides, substituted and unsubstituted anisoles and other phenol ether derivatives, substituted heterocycles, such as substituted pyridines, pyrapsines, pyrimidines, pyrrolidinones, substituted and unsubstituted N, N-di-$C_{1-2}$-alkylanilines and other fluorinated or chlorinated aromatic compounds.

A preferred solvent for the deposition of the compound according to the invention by ink-jet printing comprises a benzene derivative which contains a benzene ring which is substituted by one or more substituents, in which the total number of carbon atoms of the one or more substituents is at least three. Thus, for example, the benzene derivative may be substituted by a propyl group or three methyl groups, where in each case the total number of carbon atoms must be at least three. A solvent of this type enables the formation of an ink-jet liquid which comprises the solvent with the compound according to the invention, and reduces or prevents clogging of the nozzles and separation of the components during spraying. The solvent(s) can be selected from the following example list: dodecylbenzene, 1-methyl-4-tert-butylbenzene, terpineollimonene, isodurol, terpinolene, cymol and dethylbenzene. The solvent may also be a solvent mixture comprising two or more solvents, where each of the solvents preferably has a boiling point of greater than 100° C., more preferably greater than 140° C. Solvents of this type promote film formation of the deposited layer and reduce layer errors.

The ink-jet liquid, (i.e. a mixture, preferably of solvent(s), binder and the compound according to the invention) preferably has a viscosity at 20° C. of 1 to 100 mPa·s, more preferably 1 to 50 mPa·s and most preferably 1 to 30 mPa·s.

The compound or formation according to the invention may additionally comprise one or more further components, such as, for example, surface-active substances, lubricants, wetting agents, dispersants, water-repellent agents, adhesives, flow improvers, antifoaming agents, air deposition agents, diluents, which may be reactive or unreactive substances, assistants, colorants, dyes or pigments, sensitizers, stabilisers or inhibitors.

The invention furthermore relates to the use of the above-mentioned compounds according to the invention in one of the electronic or opto-electronic device mentioned below, such as an organic electroluminescent device, in particular an organic light-emitting diode. The compounds according to the invention are preferably formed here as or in an electroluminescent layer. A layer is preferably formed by applying a formulation according to the invention to a support and subsequently removing the solvent.

The present invention furthermore relates to an electronic device containing a compound or formulation according to the invention.

Suitable matrix materials in electronic devices are known to the person skilled in the art and can be used for the purposes of the present invention. Suitable matrix materials in electronic devices for compounds of the formula (1) are, for example, CBP (N,N-biscarbazolylbiphenyl), carbazole derivatives (for example in accordance with WO 2005/039246, US 2005/0069729, JP 2004/288381, EP 1205527 or WO 2008/086851), azacarbazoles (for example in accordance with EP 1617710, EP 1617711, EP 1731584, JP 2005/347160), ketones (for example in accordance with WO 2004/093207 or in accordance with DE 102008033943), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (for example in accordance with DE 102008017591), azaboroles or boronic esters (for example in accordance with WO 2006/117052), triazine derivatives (for example in accordance with DE 102008036982), indolocarbazole derivatives (for example in accordance with WO 2007/063754 or WO 2008/056746), indenocarbazole derivatives (for example in accordance with the unpublished application DE 102009023155.2 and DE 102009031021.5), diazaphosphole derivatives (for example in accordance with the unpublished application DE 102009022858.6), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, amino-substituted chalcone derivatives, indoles, hydrazone derivatives, stilbene derivatives, silazane derivatives, aromatic dimethylidene compounds, carbodiimide derivatives, metal complexes of 8-hydroxyquinoline derivatives, such as, for example, $AlQ_3$, the 8-hydroxyquinoline complexes may also contain triarylaminophenol ligands (US 2007/0134514 A1), metal complex polysilane compounds and thiophene, benzothiophene and dibenzothiophene derivatives.

The materials can be used as pure materials or in doped form, such as, for example, CBP intrinsic or doped with BCzVBi (=4,4'-(bis(9-ethyl-3-carbazovinylene)-1,1'-biphenyl).

It is furthermore preferred to use mixtures of two or more of the above-mentioned matrix materials, in particular mixtures of an electron-transporting material and a hole-transporting material.

Examples of preferred carbazole derivatives are mCP (=1,3-N,N-dicarbazolebenzene (=9,9'-(1,3-phenylene)bis-9H-carbazole), formula (116), US 2005/0249976), CDBP (=9,9'-(2,2'-dimethyl[1,1'-biphenyl]-4,4'-diyl)bis-9H-carbazole), 1,3-bis(N,N'-dicarbazole)benzene (=1,3-bis(carbazol-9-yl)benzene), PVK (polyvinylcarbazole), 3,5-di(9H-carbazol-9-yl)biphenyl and the further compounds having the formula (117) to (120) depicted below (see also US 2007/0128467, US 2007/0128467).

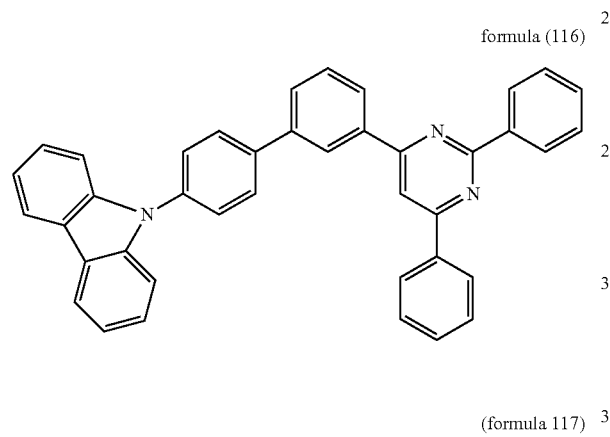

Further preferred matrix materials in the sense of the present invention are Si tetraaryls, as disclosed, for example, in US 004/209115, US 2004/0209116 US 2007/0087219, US 2007/0087219 and H. Gilman, E. A. Zuech, Chemistry & Industry (London, United Kingdom), 1960, 120, particular preference is given here to the compounds of the formulae (121) to (128).

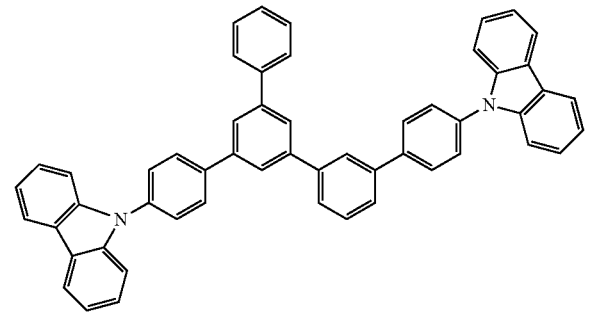
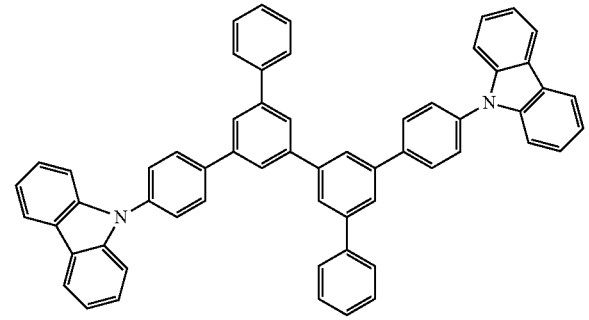
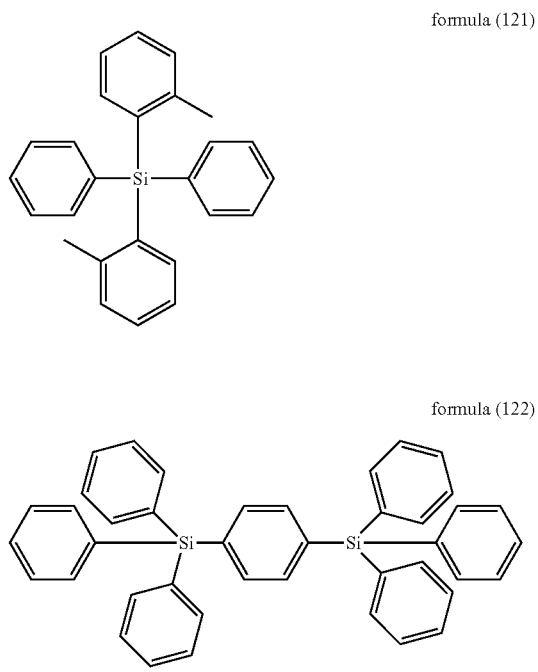

formula (123)
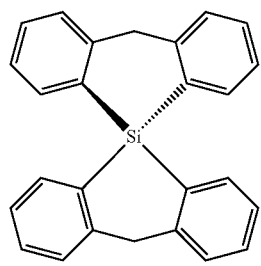
formula (124)
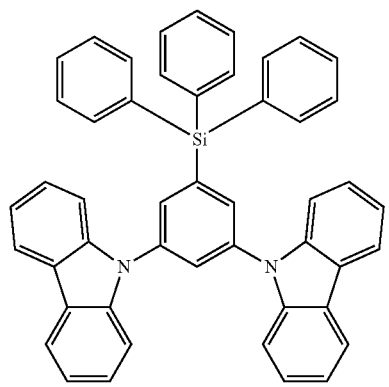
formula (125)
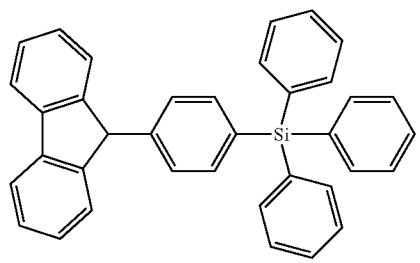
formula (126)
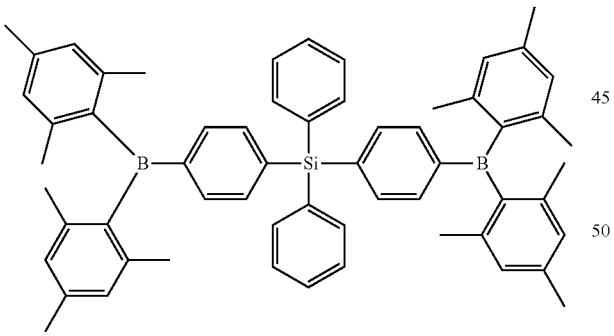
formula (127)
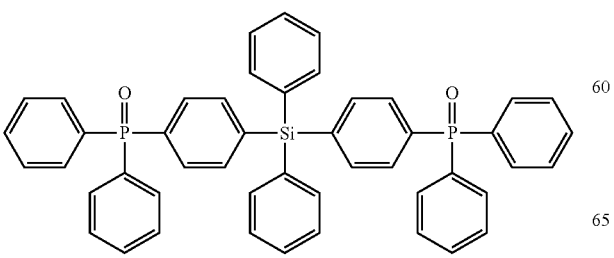
formula (128)
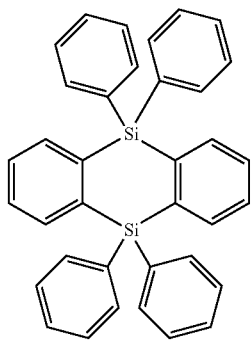
Particularly preferred matrix materials for phosphorescent dopants are compounds in EP 652273, DE 102009022858.6, DE 102009023155.2, WO 2007/063754 and WO 2008/056746, in particular the compounds of the formulae (129) to (132).
formula (129)
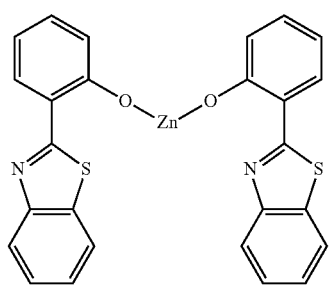
formula (130)
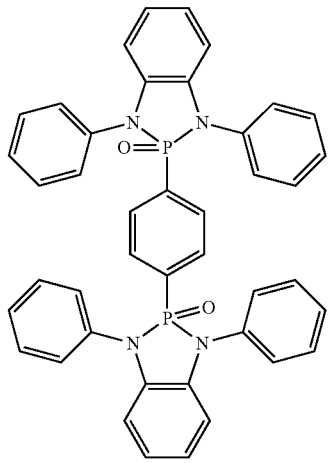
formula (131)
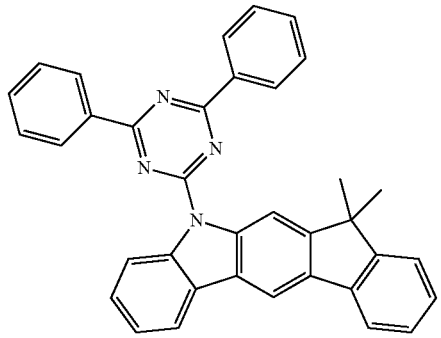

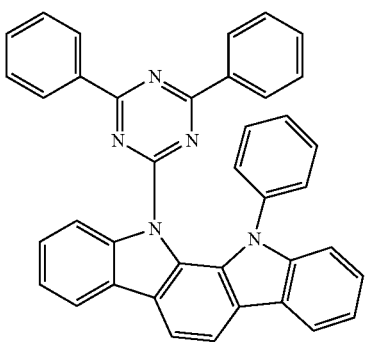

formula (132)

The electronic device is preferably an organic electroluminescent device, preferably comprising a cathode, an anode and at least one organic layer, where the organic layer comprises the compound or formulation according to the invention.

As just stated, the organic layer which comprises the compound or formulation according to the invention is preferably the emitting layer. In addition, the organic electroluminescent device may comprise further layers selected from in each case one or more hole-injection layers, hole-transport layers, hole-blocking layers, electron-transport layers, electron-injection layers, electron-blocking layers, charge-generation layers and/or layers which generate organic or inorganic P/N junctions. The electroluminescent device may in addition comprise further emitting layers. So-called interlayers, which have, for example, an exciton-blocking function, are preferably introduced between two emitting layers. However, it should be pointed out that each of these layers does not necessarily have to be present.

The organic electroluminescent device preferably has a planar shape and/or is in the form of a fibre.

A fibre in the sense of the present invention is taken to mean any shape in which the ratio between length to diameter is greater than or equal to 10:1, preferably 100:1, where the shape of the cross section along the longitudinal axis is not important. The cross section along the longitudinal axis may accordingly be, for example, round, oval, triangular, rectangular or polygonal. Light-emitting fibres have preferred properties with respect to their use. Thus, they are suitable, inter alia, for use in the area of therapeutic and/or cosmetic phototherapy. Further details in this respect are described in the prior art (for example in U.S. Pat. No. 6,538,375, US 2003/0099858, Brenndan O'Connor et al. (Adv. Mater. 2007, 19, 3897-3900 and the unpublished patent application EP 10002558.4).

If the organic electroluminescent device comprises a plurality of emitting layers, where at least one emitting layer comprises the compound according to the invention, these plurality of layers preferably have in total a plurality of emission maxima between 380 nm and 750 nm, resulting overall in white emission, i.e. various emitting compounds which are able to fluoresce or phosphoresce are used in the emitting layers. Particular preference is given to three layer systems, where the three layers exhibit blue, green and orange or red emission, for the basic structure see, for example, WO 2005/011013.

The various layers can be applied differently for the purposes of the invention. For example, one or more layers in the electroluminescent device according to the invention can be applied from solution and one or more layers can be applied via a sublimation process, in which the materials are applied by vapour deposition in vacuum sublimation units at a pressure <$10^{-5}$ mbar, preferably <$10^{-6}$ mbar, particularly preferably <$10^{-7}$ mbar. It is likewise possible to apply one or more layers by means of OVPD (organic vapour phase deposition) processes or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

However, it is particularly preferred for one or more layers in the organic electroluminescent device to be applied from solution, for example by spin coating or by means of any desired printing process, such as, for example, screen printing, flexographic printing or offset printing. But particularly preferably LITI (laser induced thermal imaging, thermal transfer printing), or ink-jet printing. These processes are generally known to the person skilled in the art and can be applied by him without problems to organic electroluminescent devices.

The device usually comprises a cathode and an anode (electrodes). The electrodes (cathode, anode) are selected for the purposes of this invention in such a way that their potential corresponds as well as possible to the potential of the adjacent organic layer in order to ensure the most efficient electron or hole injection possible.

The cathode preferably comprises metal complexes, metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides (for example LiF, $Li_2O$, $BaF_2$, MgO, NaF, etc.). The layer thickness of this layer is preferably between 1 and 10 nm, more preferably 2 to 8 nm.

The anode preferably comprises materials having a high work function. The anode preferably has a potential of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to enable either irradiation of the organic material (O-SCs) or the coupling-out of light (OLEDs/PLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive doped organic materials, in particular conductive doped polymers.

The device is correspondingly structured in a manner known per se, depending on the application, provided with contacts and finally hermetically sealed, since the lifetime of devices of this type is drastically shortened in the presence of water and/or air.

The organic electroluminescent device according to the invention is—in a non-restrictive manner—preferably selected from the group consisting of organic electroluminescent devices (OLEDs), polymeric light-emitting diodes (PLEDs), organic light-emitting electrochemical cells (OLECs), dye light-sensitive solar cells (DSSCs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors, organic laser diodes (O-lasers), radio frequency identification devices (RFID), photodetectors, sensors, logic circuits, charge-injection layers, Schottky diodes, planarizing layers, antistatic films, conductive substrates or structures, photoconductors, electrophotographic elements, organic "spintronic" devices, organic plasma-emitting devices (OPED) or organic solar concentrators. Particular preference is given to organic electroluminescent devices.

The structure of the above-mentioned electronic device is known to a person skilled in the art in the area of electronic devices. Nevertheless, some references which disclose a detailed device structure are indicated below.

An organic plasma-emitting device is preferably a device as described by Koller et al., in Nature Photonics (08), 2, pages 684 to 687. The so-called OPED is very similar to the OLED described above, apart from the fact that at least the anode or cathode should be capable of anchoring the surface plasma on the emitting layer. It is furthermore preferred for the OPED to comprise a compound according to the invention.

An organic light-emitting transistor (OLET) has a very similar structure to an organic field-effect transistor, but with a bipolar material as active layer between the source and the drain. The most recent development is revealed in a publication by Muccini et al., in Nature Materials 9, 496 to 503 (2010). Here too, it is preferred for the OLET to comprise at least one compound according to the invention.

Electrophotographic elements comprise a substrate, an electrode and a charge-transport layer above the electrode, and optionally a charge-generation layer between the electrode and the charge-transport layer. Regarding diverse details and variations of such devices and materials which can be used herein, reference is made to the book "Organic Photoreceptors for Xerography" by Marcel Dekker, Inc., Ed. by Paul M. Borsenberger & D. S. Weiss (1998). It is preferred for a device of this type to comprise a compound according to the invention, particularly preferably within a charge-transport layer.

A particularly preferred organic spintronic device is a spin-valve device, as reported by Z. H. Xiong et al., in Nature 2004 Vol. 727, page 821, which comprises two ferromagnetic electrodes and an organic layer between the two ferromagnetic electrodes, in which at least one of the organic layers, which comprises a compound according to the invention and the ferromagnetic electrode, is composed of cobalt, nickel, iron or an alloy thereof, or an ReMnO$_3$ or CrO$_2$, in which Re is a rare-earth element.

Organic light-emitting electrochemical cells (OLECs) comprise two electrodes and a mixture of electrode and fluorescent species in between, as first reported by Pei & Heeger in Science (95), 269, pages 1086 to 1088. It is desired that a compound according to the invention is used in a device of this type.

Dye-sensitized solar cells (DSSCs) comprise, in the following sequence, an electrode/a dye-sensitized TiO$_2$ porous thin film/an electrolyte/a counterelectrode, as first reported by O'Regan & Grätzel in Nature (91), 353, pages 737 to 740.

The liquid electrode may be replaced by a solid hole-transport layer, as reported in Nature (98), 395, pages 583 to 585.

Organic solar concentrators (OSC) can be used as in the report by Baldo et al., in Science 321, 226 (2008). An OSC consists of a thin film of organic dyes, which are deposited on a glass substrate having a high refractive index. The dye absorbs incident solar energy and re-emits it at low energy. The majority of the re-emitted photons are fully collected by a waveguide by total internal reflection. This takes place by means of a photovoltaic device, which is arranged at the edge of the substrate.

The compounds according to the invention and the devices comprising them are furthermore suitable for use in the area of phototherapeutic measures.

The present invention therefore furthermore relates to the use of the compounds according to the invention and devices comprising the compounds for the treatment, prophylaxis and diagnosis of diseases. The present invention still furthermore relates to the use, of the compounds according to the invention and devices comprising the compounds for the treatment and prophylaxis of cosmetic conditions.

The present invention furthermore relates to the compounds according to the invention for the production of devices for the therapy, prophylaxis and/or diagnosis of therapeutic diseases.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) and disinfection and sterilisation in general. Phototherapy or light therapy can be used for the treatment of not only humans or animals, but also any other type of living or non-living materials. These include, for example, fungi, bacteria, microbes, viruses, eukaryotes, prokaryonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. However, the treatment or irradiation according to the invention can also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photo-modulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitization of the skin.

Particular preference is given for the purposes of the invention to the treatment and/or prophylaxis of psoriasis, acne, cellulite, skin wrinkling, skin ageing, icterus and vitiligo.

Further areas of application according to the invention for the compositions and/or devices comprising the compositions according to the invention are selected from the group of inflammatory diseases, rheumatoid arthritis, pain therapy, treatment of wounds, neurological diseases and conditions, oedema, Paget's disease, primary and metastasizing tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds and/or devices comprising the compounds according to the invention are selected from winter depression, sleeping sickness, irradiation for improving the mood, the reduction in pain particularly muscular pain caused by, for example, tension or joint pain, elimination of joint stiffness and the whitening of the teeth (bleaching).

Further areas of application according to the invention for the compounds and/or devices comprising the compounds according to the invention are selected from the group of disinfections. The compounds according to the invention and/or the devices according to the invention can be used for the treatment of any type of objects (non-living materials) or subjects (living materials such as, for example, humans and animals) for the purposes of disinfection. This includes, for example, the disinfection of wounds, the reduction in bacteria, the disinfection of surgical instruments or other articles, the disinfection of foods, of liquids, in particular water, drinking water and other drinks, the disinfection of mucous membranes and gums and teeth. Disinfection here is taken to mean the reduction in the living microbiological causative agents of undesired effects, such as bacteria and germs.

For the purposes of the above-mentioned phototherapy, devices containing the compounds according to the invention preferably emit light having a wavelength between 250 and 1250 nm, particularly preferably between 300 and 1000 nm and especially preferably between 400 and 850 nm.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for reuse or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The present invention furthermore relates to a method for the therapy, prophylaxis and/or diagnosis of diseases, where the compounds and devices according to the invention are used for this purpose.

The present invention furthermore relates to a method for the therapy, prophylaxis and/or diagnosis of cosmetic conditions, where the compounds and devices according to the invention are used for this purpose.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

EXAMPLES

The following syntheses are carried out, unless indicated otherwise, under a protective-gas atmosphere in dried solvents. The starting materials and solvents are commercially available, for example from Merck.
Compound I can be prepared in accordance with the synthesis indicated in DE 102009023154.4. Compounds III and VI can be prepared analogously to WO 2002/068435.
Example 1
Preparation of Compound VII
Compound VII is prepared in accordance with the following reaction scheme:
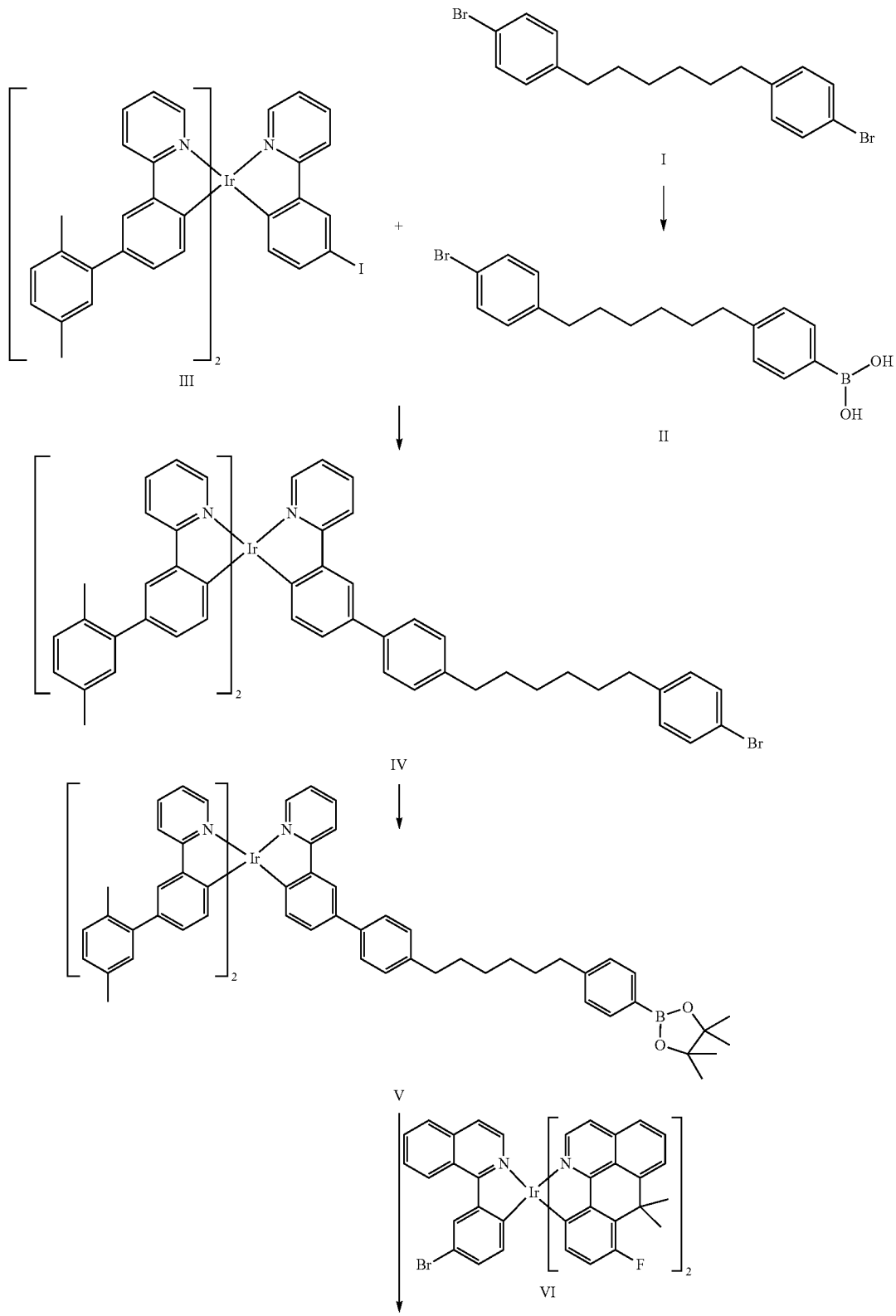

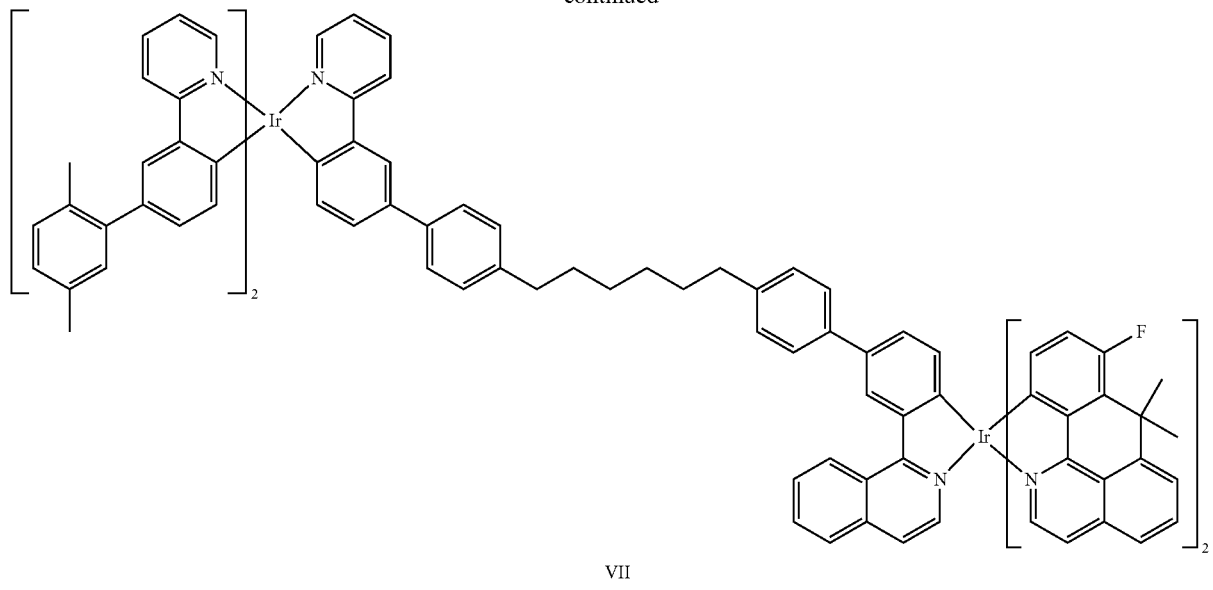

VII a) Synthesis of Compound II

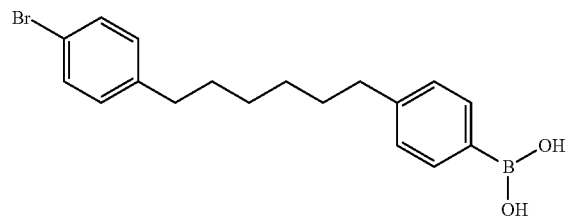

II 101.2 g (0.26 mol) of compound I are initially introduced in 1600 ml of THF and cooled to −75° C. in an acetone/dry-ice bath. 124 ml (0.31 mol) of n-butyllithium (2.5 M in hexane) are added dropwise at such a rate that the internal temperature does not exceed −69° C., the mixture is subsequently stirred at −72° C. for a further 2 hours. 43.5 ml (0.39 mol) of trimethyl borate are then dissolved in 400 ml of THF and slowly added dropwise at −72° C. at such a rate that the internal temperature does not exceed −69° C. The reaction solution is stirred at −70° C. for a further hour and at room temperature overnight. 300 ml of hydrochloric acid (10%) are added to the batch. The phases are separated. The aqueous phase is extracted with dichloromethane (DCM). The combined organic phases are washed with water, dried over $Na_2SO_4$, filtered and evaporated under reduced pressure. The residue is washed with ethanol and recrystallised from heptane. The yield is 65.3 g (0.18 mol), corresponding to 70.8% of theory.

b) Synthesis of Compound IV

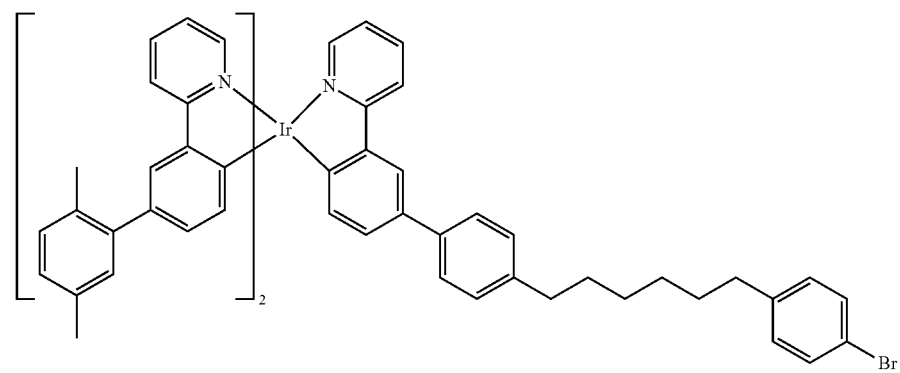

IV 21.2 g (21 mmol) of compound III, 9.7 g (27 mmol) of compound II and 29.6 g (140 mmol) of K₃PO₄ are suspended in 500 ml of toluene, 500 ml of dioxane and 500 ml of water. 51 mg (0.22 mmol) of Pd(OAc)₂ and 0.68 g (2.2 mmol) of tri-o-tolylphosphine are added to this suspension. The reaction mixture is heated under reflux for 42 h. After cooling, the organic phase is separated off, washed three times with 500 ml of water and subsequently evaporated to dryness. The residue is washed with ethanol and finally dried under reduced pressure. The yield is 12.2 g (10 mmol), corresponding to 46.0% of theory.

c) Synthesis of Compound V 500 ml of dioxane, 2.8 g (11.0 mmol) of bis(pinacolato)diborane in 100 ml of dioxane, 2.9 g (30.0 mmol) of potassium acetate in 100 ml of dioxane and 0.41 g (0.5 mmol) of 1,1-bis(diphenylphosphine)ferrocenepalladium (II) chloride (complex with dichloromethane (1:1), Pd: 13%) are added to 11.8 g (10.0 mmol) of compound IV. The batch is stirred at 80° C. for 3 h, and 500 ml of ice-water are slowly added dropwise. The aqueous phase is extracted by shaking three times with DCM. The organic phases are combined, dried over Na₂SO₄, filtered and evaporated in a rotary

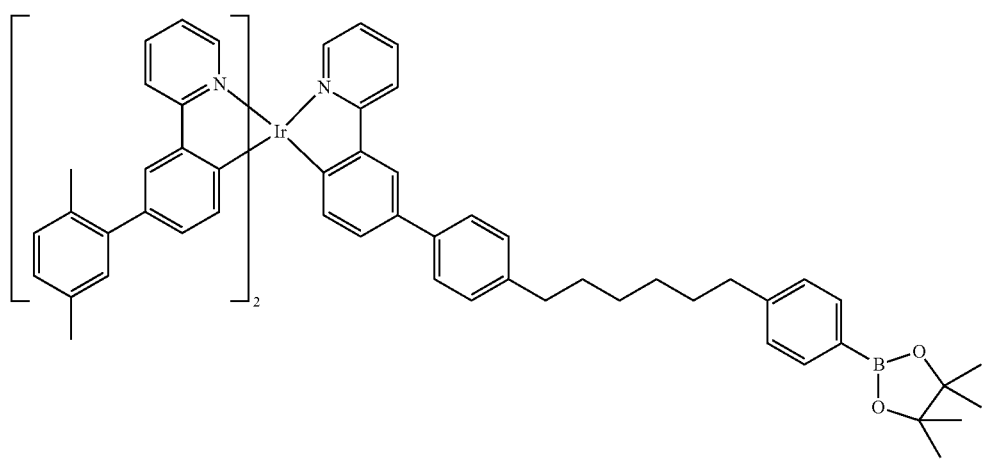

V evaporator. The residue is washed with ethanol, acetonitrile and heptane and finally dried under reduced pressure. The yield is 9.4 g (7.9 mmol), corresponding to 79.0% of theory.

d) Synthesis of Compound VII

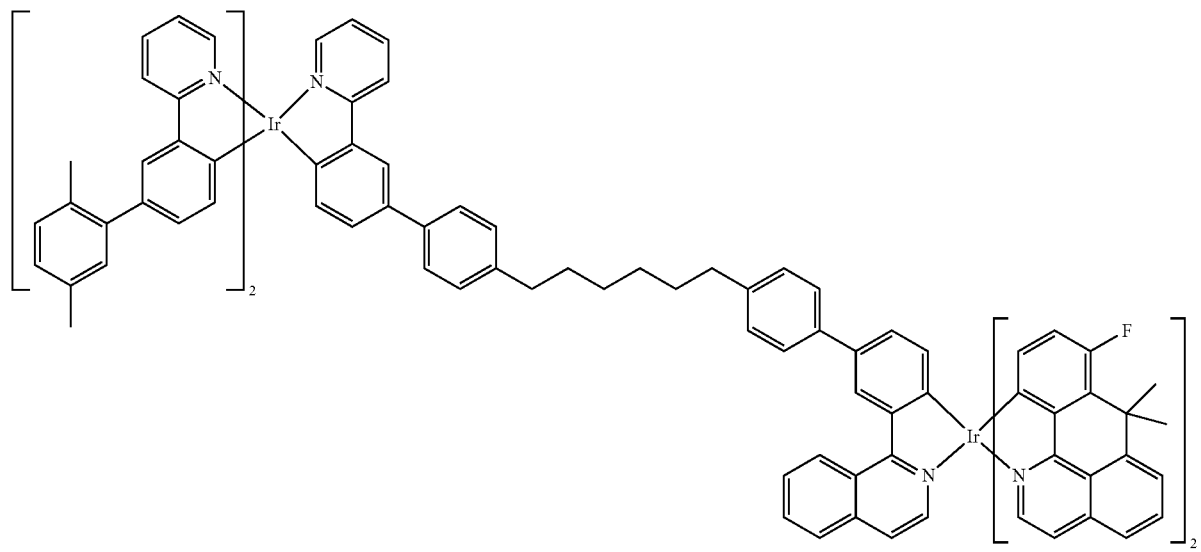

VII 9.2 g (7.0 mmol) of compound V, 6.8 g (6.8 mmol) of compound VI and 8.9 g (42.2 mmol) of $K_3PO_4$ are suspended in 250 ml of toluene, 250 ml of dioxane and 250 ml of water. 15 mg (0.07 mmol) of $Pd(OAc)_2$ and 0.21 g (0.68 mmol) of tri-o-tolylphosphine are added to this suspension. The reaction mixture is heated under reflux for 42 h. After cooling, the organic phase is separated off, washed three times with 125 ml of water and subsequently evaporated to dryness. The residue is washed with ethanol and recrystallised from toluene and finally dried under reduced pressure. The yield is 4.2 g (2.1 mmol), corresponding to 30.6% of theory.

Example 2

Production and Characterisation of Organic Electroluminescent Devices Containing the Compounds According to the Invention The structures of emitters E1 (synthesised in accordance with WO 2004/026886) and E2 (synthesised in accordance with WO 2005/033244), compound E3 according to the invention, and matrix compound M1 (synthesised in accordance with WO 2004/093207) are depicted below for clarity.

Structures of the Compounds

The production of an organic light-emitting diode from solution has already been described many times in the literature (for example in WO 2004/037887 A2) and is well known to the person skilled in the art. In order to explain the present invention by way of example, triplet OLEDs with various combinations of E1-E3 in matrix M1 are produced by means of spin coating.

A typical OLED device has the following structure: cathode/EML-emissive layer/interlayer/HIL-hole injection layer/anode (ITO), where HIL is also referred to as buffer layer.

To this end, use is made of substrates from Technoprint (soda-lime glass) to which the ITO structure (indium tin oxide, a transparent, conductive anode) is applied.

The substrates are cleaned in a clean room with DI (deionised) water and a detergent (Deconex 15 PF) and then activated by UV/ozone plasma treatment. An 80 nm layer of PEDOT (PEDOT is a polythiophene derivative (Baytron P VAI 4083sp.) from H. C. Starck, Goslar, which is supplied as an aqueous dispersion) is then applied as buffer layer by spin coating, likewise in the clean room. The requisite spin rate depends on the degree of dilution and the specific spin-coater geometry (typical for 80 nm: 4500 rpm). In order

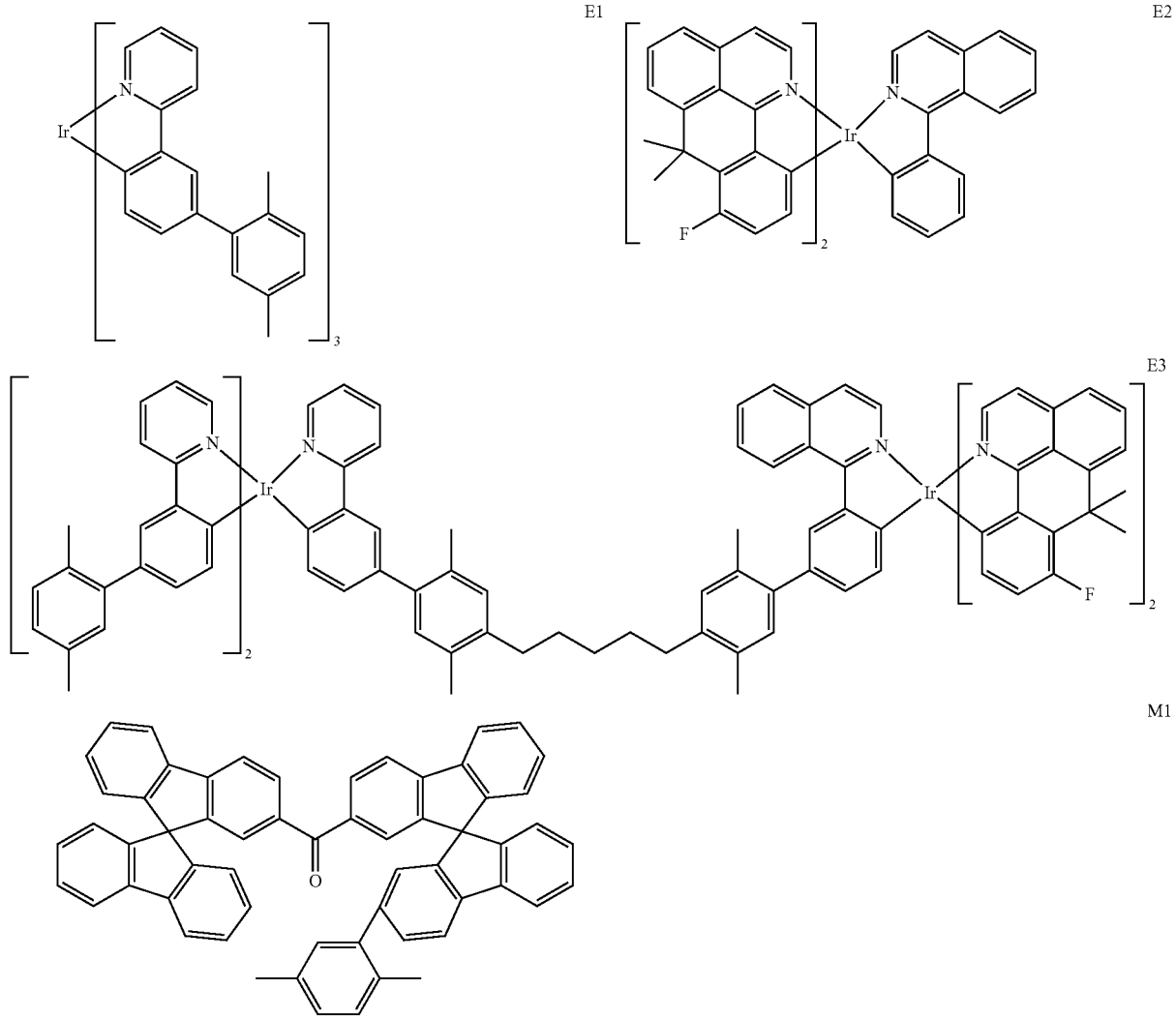

to remove residual water from the layer, the substrates are dried by heating on a hotplate at 180° C. for 10 minutes. Then, under inert-gas atmosphere (nitrogen or argon), firstly 20 nm of an interlayer (typically a hole-dominated polymer P1) and then 80 nm of the emitting layer (EML for emissive layer) are applied from solutions (concentration 20 g/l in chlorobenzene, the compositions for the various EMLs, and the concentrations thereof are listed in Table 1). The interlayer polymer P1 used is HIL-012 from Merck KGaA, Germany. All EML layers are dried by heating at 180° C. for at least 10 minutes. The Ba/Al cathode is then applied by vapour deposition (high-purity metals from Aldrich, particularly barium 99.99% (Order No. 474711); vapour-deposition units from Lesker or others, typical vacuum level $5 \times 10^6$ mbar). In order to protect, in particular, the cathode against air and atmospheric moisture, the device is finally encapsulated and then characterised.

TABLE 1

The EML compositions in various OLEDs

| Device | EML composition [wt %] | Solvent | Concentration [g/l] |
|---|---|---|---|
| OLED1 | M1: 10% E2 | Chlorobenzene | 20 |
| OLED2 | M1: 10% E1: 10% E2 | Chlorobenzene | 20 |
| OLED3 | M1: 10% E3 | Chlorobenzene | 20 |

To this end, the devices are clamped into holders manufactured especially for the substrate size and provided with spring contacts. A photodiode with eye response filter can be attached directly to the measurement holder in order to exclude influences by extraneous light. A typical measurement set-up is depicted in Figure 1.

The voltages are typically increased from 0 to max. 20 V in 0.2 V steps and reduced again. For each measurement point, the current through the device and the photocurrent obtained from the photodiode is measured. In this way, the IVL data of the test devices are obtained. Important characteristic quantities are the measured maximum efficiency ("eff." in cd/A) and the voltage $U_{100}$ required for 100 cd/m².

In order, in addition, to know the colour and the precise electroluminescence spectrum of the test devices, the voltage required for 100 cd/m² is again applied after the first measurement, and the photodiode is replaced by a spectrum-measuring head. This is connected to a spectrometer (Ocean Optics) by an optical fibre. The colour coordinates (CIE: Commission International de l'éclairage, 1931 standard observer) can be derived from the measured spectrum.

The results obtained on use of emitters E1 to E3 in OLEDs are summarized in Table 2.

TABLE 2

| Device | Max. eff. [cd/A] | Uon [V] | U(100) [V] | CIE @ 100 cd/m² | EQE @ max. eff. | LT @ 1 k nits [hrs] |
|---|---|---|---|---|---|---|
| OLED1 | 6.0 | 3.3 | 5.7 | 0.64/0.35 | 4.9% | 30 |
| OLED2 | 6.9 | 3.2 | 5.6 | 0.62/0.37 | 5.4% | 150 |
| OLED3 | 8.7 | 3.3 | 5.4 | 0.64/0.35 | 7.3% | 900 |

As can be seen from the results, OLED2 and OLED3 represent a significant improvement compared with OLED1 with respect to the efficiency and lifetime. In OLED2, the principle of double doping known in the prior art is utilised, where the two triplet emitters E1 and E2 are simultaneously doped into the matrix, and the energy transfer, such as, for example, in accordance with Förster, takes place from E1 to E2. A significant improvement in the lifetime from 30 h (in the case of OLED1) to 150 h (in the case of OLED2) is additionally achieved. The mechanism of this type of "double doping" was described in the article by Kawamura, Y. et al., J. Appl. Phys. 92[1], 87-93. 2002. OLED3, in which emitter E3 according to the invention is used, has again shown a significant improvement compared with OLED2, both with respect to the efficiency and also the lifetime. The cause of this is the efficient energy transfer by the Förster mechanism of emitting units in E3 connected by the covalent bond. On the basis of the present technical teaching according to the invention, it will be possible to achieve further optimizations by means of different possibilities without being inventive. Thus, a further optimisation can be achieved, for example through the use of another matrix or mixed matrices in the same or a different concentration.

The invention claimed is:

1. A compound of the following formula

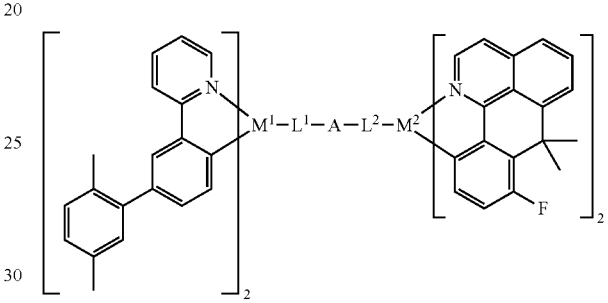

where
A is a divalent unit which contains a conjugation-interrupting unit;
$M^1$ and $M^2$ are, independently of one another and identically or differently on each occurrence, selected from the group consisting of the main-group metals, transition metals, lanthanoids and actinoids;
$L^1$ and $L^2$ are, independently of one another, and with the metal form a cyclometallated five-membered ring or six-membered ring having at least one metal-carbon bond.

2. The compound according to claim 1, wherein $M^1$ and $M^2$ are selected, independently of one another and identically or differently on each occurrence, from the group consisting of Ir, Ru, Os, Eu, Pt, Zn, Mo, W, Rh and Pd.

3. The compound according to claim 1, wherein A is a divalent unit selected from the group consisting of the following:
linear or branched $C_{1-12}$-alkylene,
$C_{3-8}$-cycloalkylene,
linear or branched mono($C_{1-12}$-alkyl)silylene,
linear or branched di($C_{1-12}$-alkyl)silylene,
linear or branched tri($C_{1-12}$-alkyl)silylene,
a silylene group which is substituted by one, two or three mono- or polycyclic aromatic or heteroaromatic ring systems having 5 to 60 aromatic ring atoms,
linear or branched Si1-5-silylene,
linear or branched C1-12-alkyloxy-C1-12-alkylene,
linear or branched aryl-C1-12-alkyloxy-C1-12-alkylene, where aryl is a mono- or polycyclic aromatic or heteroaromatic ring system having 5 to 60 aromatic ring atoms,
linear or branched C1-12-alkylthio-C1-12-alkylene,
sulfone,
linear or branched C1-12-alkylene sulfone, sulfone oxide and
linear or branched $C_{1-12}$-alkylene sulfone oxide,
where one or more H atoms of the said groups which represent A is optionally replaced by F, Cl, Br, I, a further $C_{1-12}$-alkyl or $C_{3-8}$-cycloalkyl, where one or more $CH_2$ groups of the alkyl or cycloalkyl is optionally replaced by heteroatoms, or a mono- or polycyclic aromatic or heteroaromatic ring system having 5 to 60 aromatic ring atoms, and
where one or more $CH_2$ groups of the said groups which represent A is optionally replaced by a divalent mono- or polycyclic aromatic or heteroaromatic ring system having 5 to 60 aromatic ring atoms, and
with the proviso that the divalent unit A can bond to the ligands $L^1$ or $L^2$ via any conceivable atom of the unit.

4. The compound according to claim 1, wherein in each case $L^1$ and $L^2$ is a bidentate ligand independently selected from phenylpyridine, naphthylpyridine, phenylquinoline, or phenylisoquinoline, wherein each of which is optionally substituted by one or more radicals R
wherein R is alkyl(ene), cycloalkyl(ene), alkylsilyl(ene), silyl(ene), arylsilyl(ene), alkylalkoxyalkyl(ene), arylalkoxyalkyl(ene), alkylthioalkyl(ene), phosphine, phosphine oxide, sulfone, alkylene sulfone, sulfone oxide, alkylene sulfone oxide, where the alkylene group in each case, independently of one another, has 1 to 12 carbon atoms and where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

5. The compound according to claim 1, wherein

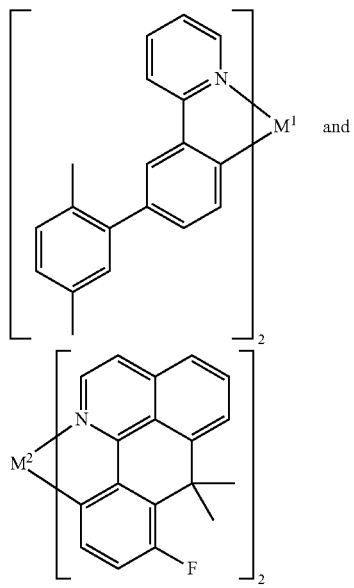

are phosphorescent compounds.

6. An electronic device comprising the compound according to claim 1.

7. An organic electroluminescent device containing a the compound according to claim 1, wherein the device is an organic light-emitting diode, an organic light-emitting electrochemical cell or an organic light-emitting transistor.

8. The organic electroluminescent device according to claim 7, wherein the device has a planar shape and/or is in the form of a fibre.

9. An electronic device comprising the compound according to claim 1, wherein the device is selected from the group consisting of an organic integrated circuit, an organic field-effect transistor, an organic thin-film transistor, an organic solar cell, a dye-sensitised organic solar cell, an organic optical detector, an organic photoreceptor, an organic field-quench device, an organic laser diode and an organic plasmon emitting device.

10. A formulation comprising at least one compound according to claim 1 and at least one solvent.

11. The formulation according to claim 10, wherein the formulation is a solution, dispersion or emulsion.

12. A compound according to claim 1 for the therapy, prophylaxis and/or diagnosis of diseases and/or cosmetic conditions.

13. The compound according to claim 1, wherein A is a divalent unit selected from the group consisting of the following:
linear or branched $C_{1-12}$-alkylene,
$C_{3-8}$-cycloalkylene,
linear or branched C1-12-alkyloxy-C1-12-alkylene,
linear or branched aryl-C1-12-alkyloxy-C1-12-alkylene,
where aryl is a mono- or polycyclic aromatic or heteroaromatic ring system having 5 to 60 aromatic ring atoms,
linear or branched C1-12-alkylthio-C1-12-alkylene,
sulfone,
linear or branched C1-12-alkylene sulfone,
and one or more H atoms of the said groups which represent A is optionally replaced by F, Cl, Br, I, or a further $C_{1-12}$-alkyl or $C_{3-8}$-cycloalkyl,
where one or more $CH_2$ groups of the alkyl or cycloalkyl is optionally replaced by heteroatoms, or a mono- or polycyclic aromatic or heteroaromatic ring system having 5 to 60 aromatic ring atoms, and
where one or more $CH_2$ groups of the said groups which represent A is optionally replaced by a divalent mono- or polycyclic aromatic or heteroaromatic ring system having 5 to 60 aromatic ring atoms.

14. The compound according to claim 1, wherein A is of formula (18)

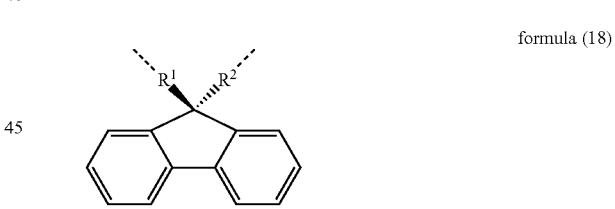

formula (18)

wherein $R^1$ and $R^2$ are independently selected from alkylene, cycloalkylene, alkylsilylene, silylene, arylsilylene, alkylalkoxyalkylene, arylalkoxyalkylene, alkylthioalkylene, phosphine, phosphine oxide, sulfone, alkylene sulfone, sulfone oxide, alkylene sulfone oxide, where the alkylene group in each case, independently of one another, has 1 to 12 carbon atoms and where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

15. The compound according to claim 14, wherein $R^1$ and $R^2$ are both phenylene.

16. The compound according to claim 14, wherein in each case $L^1$ and $L^2$ is a bidentate ligand independently selected from phenylpyridine, naphthylpyridine, phenylquinoline, or phenylisoquinoline.

17. A compound of the following formula

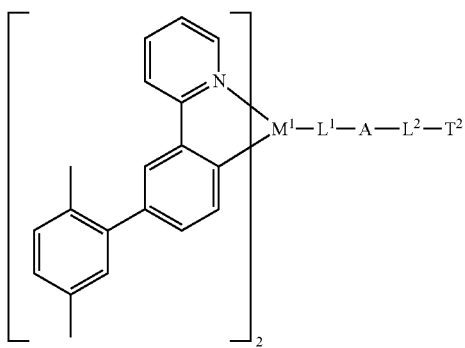 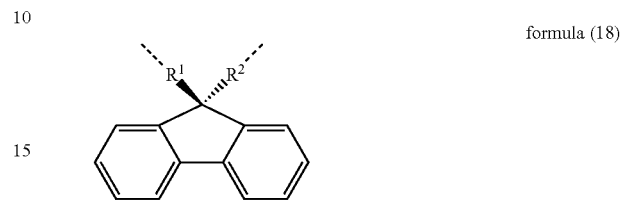

where
A is a divalent unit which contains a conjugation-interrupting unit;
$T^2$ is a monovalent unit of the formula $M^2L'_2$;
$M^1$ and $M^2$ are independently selected from the group consisting of the main-group metals, transition metals, lanthanoids and actinoids;
L', $L^1$ and $L^2$ are, independently of one another, and together with $M^1$ and $M^2$, respectively, have a cyclo-metallated five-membered ring or six-membered ring having at least one metal-carbon bond.

18. The compound according to claim 17, wherein in each case $L^1$ and $L^2$ is a bidentate ligand independently selected from phenylpyridine, naphthylpyridine, phenylquinoline, or phenylisoquinoline, wherein each of which is optionally substituted by one or more radicals R
wherein R is alkyl(ene), cycloalkyl(ene), alkylsilyl(ene), silyl(ene), arylsilyl(ene), alkylalkoxyalkyl(ene), arylalkoxyalkyl(ene), alkylthioalkyl(ene), where the alkylene group in each case, independently of one another, has 1 to 12 carbon atoms and where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

19. The compound according to claim 17, wherein A is of formula (18)

formula (18)

wherein $R^1$ and $R^2$ are independently selected from alkylene, cycloalkylene, alkylsilylene, silylene, arylsilylene, alkylalkoxyalkylene, arylalkoxyalkylene, alkylthioalkylene, phosphine, phosphine oxide, sulfone, alkylene sulfone, sulfone oxide, alkylene sulfone oxide, where the alkylene group in each case, independently of one another, has 1 to 12 carbon atoms and where one or more H atoms may be replaced by F, Cl, Br, I, alkyl or cycloalkyl, where one or more $CH_2$ may be replaced by a heteroatom, such as NH, O or S, or an aromatic or heteroaromatic hydrocarbon radical having 5 to 20 aromatic ring atoms.

20. The compound according to claim 19, wherein $R^1$ and $R^2$ are both phenyl, and in each case $L^1$ and $L^2$ is a bidentate ligand independently selected from phenylpyridine, naphthylpyridine, phenylquinoline, or phenylisoquinoline.

21. The device according to claim 6 for the therapy, prophylaxis and/or diagnosis of diseases and/or cosmetic conditions.

* * * * *